United States Patent
Ahl et al.

(10) Patent No.: US 12,144,855 B2
(45) Date of Patent: Nov. 19, 2024

(54) METHODS FOR PRODUCING STREPTOCOCCUS PNEUMONIAE CAPSULAR POLYSACCHARIDE CARRIER PROTEIN CONJUGATES FROM LYOSPHERES

(71) Applicant: Merck Sharp & Dohme LLC, Rahway, NJ (US)

(72) Inventors: Patrick Leonard Ahl, West Point, PA (US); Akhilesh Bhambhani, Doylestown, PA (US); Christopher Jon Farrell, Wayne, PA (US); Patrick McHugh, Pipersville, PA (US); Morrisa C. Jones, Upper Darby, PA (US); Daniel D. Roth, Coopersburg, PA (US); Jessica R. Sinacola, Collegeville, PA (US); Justin Stanbro, Sellersville, PA (US); Matthew P. Watson, Ottsville, PA (US); Emily Wen, Harleysville, PA (US); Michael A. Winters, Doylestown, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 997 days.

(21) Appl. No.: 17/049,208

(22) PCT Filed: Apr. 25, 2019

(86) PCT No.: PCT/US2019/029034
§ 371 (c)(1),
(2) Date: Oct. 20, 2020

(87) PCT Pub. No.: WO2019/212842
PCT Pub. Date: Nov. 7, 2019

(65) Prior Publication Data
US 2021/0236646 A1    Aug. 5, 2021

Related U.S. Application Data

(60) Provisional application No. 62/664,621, filed on Apr. 30, 2018.

(51) Int. Cl.
| | |
|---|---|
| A61K 39/02 | (2006.01) |
| A61K 9/19 | (2006.01) |
| A61K 39/09 | (2006.01) |
| A61K 39/116 | (2006.01) |
| A61K 47/61 | (2017.01) |
| A61K 47/64 | (2017.01) |
| A61K 47/68 | (2017.01) |
| A61K 47/69 | (2017.01) |
| A61K 39/00 | (2006.01) |

(52) U.S. Cl.
CPC .............. *A61K 39/116* (2013.01); *A61K 9/19* (2013.01); *A61K 39/092* (2013.01); *A61K 47/61* (2017.08); *A61K 47/6415* (2017.08); *A61K 47/6829* (2017.08); *A61K 47/6921* (2017.08); *A61K 2039/6031* (2013.01); *A61K 2039/6037* (2013.01); *A61K 2039/70* (2013.01); *A61K 47/646* (2017.08)

(58) Field of Classification Search
None
See application file for complete search history.

(56) References Cited

U.S. PATENT DOCUMENTS

| | | |
|---|---|---|
| 6,146,902 A | 11/2000 | McMaster |
| 6,517,526 B1 | 2/2003 | Tamari |
| 7,709,001 B2 | 5/2010 | Hausdorff et al. |
| 8,808,707 B1 | 8/2014 | Siber |
| 9,669,084 B2 | 6/2017 | Siber |
| 10,406,220 B2 | 9/2019 | Siber et al. |
| 2007/0042031 A1 | 2/2007 | MacLachlan et al. |
| 2007/0231340 A1 | 10/2007 | Hausdorff et al. |
| 2009/0010966 A1 | 1/2009 | Davis et al. |

(Continued)

FOREIGN PATENT DOCUMENTS

| | | |
|---|---|---|
| CN | 102068690 A | 5/2011 |
| EP | 3096786 B1 | 7/2021 |

(Continued)

OTHER PUBLICATIONS

Arditi et al., Three-Year Multicenter Surveillance of Pneumococcal Meningitis in Children: Clinical Characteristics, and Outcome Related to Penicillin Susceptibility and Dexamethasone Use, Pediatrics, 1998, 1087-1097, 102(5).

Lei et al., Quantification of free polysaccharide in meningococcal polysaccharide-diphtheria toxoid conjugate vaccines, Dev. Biol., 2000, Abstract—1/1, 103.

(Continued)

*Primary Examiner* — Jennifer E Graser
(74) *Attorney, Agent, or Firm* — Jonathan Fitzgerald; Catherine D. Fitch (57) ABSTRACT

A method is described for producing a pneumococcal capsular polysaccharide protein conjugate in which one or more activated pneumococcal polysaccharides of particular pneumococcal serotypes and carrier protein are separately lyophilized in the form of lyospheres of carrier protein and lyospheres of the one or more polysaccharides. A predetermined amount of carrier protein lyospheres and activated polysaccharide lyospheres are mixed together and the mixture reconstituted in an organic solvent to produce polysaccharide carrier protein conjugates. A plurality of conjugates, each comprising polysaccharides of a particular serotype, may be used to produce multivalent pneumococcal immunogenic compositions having a combination of conjugates for use in vaccines.

13 Claims, 1 Drawing Sheet

(56) References Cited

U.S. PATENT DOCUMENTS

| | | |
|---|---|---|
| 2011/0195086 A1 | 8/2011 | Caulfield et al. |
| 2011/0201791 A1 | 8/2011 | Prasad |
| 2012/0045479 A1 | 2/2012 | Sievers et al. |
| 2015/0190521 A1 | 7/2015 | Biemans et al. |
| 2015/0202309 A1 | 7/2015 | Emini et al. |
| 2016/0009768 A1 | 1/2016 | Davis et al. |
| 2016/0252300 A1 | 9/2016 | Bhambhani et al. |
| 2016/0324948 A1 | 11/2016 | Gu et al. |
| 2016/0324950 A1 | 11/2016 | Anderson et al. |
| 2017/0220463 A1 | 8/2017 | Malina et al. |
| 2018/0099039 A1 | 4/2018 | Emini et al. |

FOREIGN PATENT DOCUMENTS

| | | |
|---|---|---|
| WO | 200038711 A2 | 7/2000 |
| WO | 2006110352 A2 | 10/2006 |
| WO | 2006110381 A1 | 10/2006 |
| WO | 2007127665 A2 | 11/2007 |
| WO | 2008045852 A2 | 4/2008 |
| WO | 2008118752 A2 | 10/2008 |
| WO | 2009009629 A1 | 1/2009 |
| WO | 2010080484 A1 | 7/2010 |
| WO | 2010080486 A2 | 7/2010 |
| WO | 2011041003 A2 | 4/2011 |
| WO | 2011100151 A1 | 8/2011 |
| WO | 2011151760 A2 | 12/2011 |
| WO | 2012078482 A1 | 6/2012 |
| WO | 2014097099 A2 | 6/2014 |
| WO | 2015110940 A2 | 7/2015 |
| WO | 2015110941 A2 | 7/2015 |
| WO | 2015110942 A2 | 7/2015 |
| WO | 2016113644 A1 | 7/2016 |
| WO | 2016178123 A1 | 11/2016 |
| WO | 2017013548 A1 | 1/2017 |
| WO | 2017085586 A1 | 5/2017 |
| WO | 2017085602 A1 | 5/2017 |
| WO | 2018134693 A1 | 7/2018 |
| WO | 2018144438 A1 | 8/2018 |
| WO | 2018144439 A1 | 8/2018 |
| WO | 2018156465 A1 | 8/2018 |
| WO | 2018156467 A1 | 8/2018 |
| WO | 2018156468 A1 | 8/2018 |
| WO | 2018156491 A1 | 8/2018 |
| WO | 2018212846 A1 | 11/2018 |
| WO | 2019036313 A1 | 2/2019 |
| WO | 2019050813 A1 | 3/2019 |
| WO | 2019050814 A1 | 3/2019 |
| WO | 2019050815 A1 | 3/2019 |
| WO | 2019050816 A1 | 3/2019 |
| WO | 2019050818 A1 | 3/2019 |
| WO | 2019083865 A1 | 5/2019 |
| WO | 2019139692 A2 | 7/2019 |
| WO | 2019212842 A1 | 11/2019 |
| WO | 2019212844 A1 | 11/2019 |
| WO | 2019212846 A1 | 11/2019 |
| WO | 2019217183 A1 | 11/2019 |
| WO | 2019236435 A1 | 12/2019 |
| WO | 2020121159 A1 | 6/2020 |
| WO | 2020131763 A2 | 6/2020 |
| WO | 2020208502 A1 | 10/2020 |
| WO | 2020247299 A1 | 12/2020 |
| WO | 2020247301 A1 | 12/2020 |

OTHER PUBLICATIONS

MMWR, Prevention of Pneumococcal Disease: Recommendations of the Advisory Committee on Immunization Practices (ACIP), Centers for Disease Control and Prevention, 1997, 1-25, 46(RR-8).

Shivu, Bhavana, Distinct /J-Sheet Structure in Protein Aggregates Determined by ATR-FTIR Spectroscopy, Biochemistry, 2013, 5176-5183, 52.

Lei, Q.P. et al., Quantification of Free Polysaccharide in Meningococcal Polysaccharide-Diphtheria Toxoid Conjugate Vaccines, Dev. Biol., 2000, 259-264, 103.

Nagaki, Aiichiro et al., Fast Micromixing and Flow Synthesis, Nagare: Journal of Japan Society of Fluid Mechanics, 2015, 3-9, 34.

Steven P. Schwendeman et al., Stabilization of tetanus and diphtheria toxoids against moisture-induced aggregation, Proc. Natl. Acad. Sci. USA, 1995, 11234-11238, 92.

METHODS FOR PRODUCING STREPTOCOCCUS PNEUMONIAE CAPSULAR POLYSACCHARIDE CARRIER PROTEIN CONJUGATES FROM LYOSPHERES

BACKGROUND OF THE INVENTION

(1) Field of the Invention

The present invention relates to a method for producing a pneumococcal capsular polysaccharide carrier protein conjugate in which one or more activated pneumococcal polysaccharides of particular pneumococcal serotypes and carrier protein are separately lyophilized in the form of lyospheres of carrier protein and lyospheres of the one or more activated polysaccharides. A predetermined amount of carrier protein lyospheres and activated polysaccharide lyospheres are mixed together and the mixture reconstituted in an organic solvent to produce polysaccharide carrier protein conjugates. A plurality of conjugates, each comprising polysaccharides of a particular serotype, may be used to produce multivalent pneumococcal immunogenic compositions having a combination of conjugates for use in vaccines.

(2) Description of Related Art

*Streptococcus pneumoniae*, one example of an encapsulated bacterium, is a significant cause of serious disease world-wide. In 1997, the Centers for Disease Control and Prevention (CDC) estimated there are 3,000 cases of pneumococcal meningitis, 50,000 cases of pneumococcal bacteremia, 7,000,000 cases of pneumococcal otitis media and 500,000 cases of pneumococcal pneumonia annually in the United States. See Centers for Disease Control and Prevention, MMWR Morb Mortal Wkly Rep 1997, 46(RR-8):1-13. Furthermore, the complications of these diseases can be significant with some studies reporting up to 8% mortality and 25% neurologic sequelae with pneumococcal meningitis. See Arditi et al., 1998, Pediatrics 102:1087-97.

The multivalent pneumococcal polysaccharide vaccines that have been licensed for many years have proved invaluable in preventing pneumococcal disease in adults, particularly, the elderly and those at high-risk. However, infants and young children respond poorly to unconjugated pneumococcal polysaccharides. Bacterial polysaccharides are T-cell-independent immunogens, eliciting weak or no response in infants. Chemical conjugation of a bacterial polysaccharide immunogen to a carrier protein converts the immune response to a T-cell-dependent one in infants. Diphtheria toxoid (DTx, a chemically detoxified version of DT) and $CRM_{197}$ have been described as carrier proteins for bacterial polysaccharide immunogens due to the presence of T-cell-stimulating epitopes in their amino acid sequences.

Thus, polysaccharide-protein conjugate vaccines, comprising bacterial capsular polysaccharides conjugated to carrier proteins have been developed and additional ones are in development. Examples of developed conjugate vaccines include the *Haemophilus influenzae* type b (Hib) conjugate vaccine (e.g., HIBTITER®) as well as conjugate vaccines against *Streptococcus pneumoniae* (e.g., PREVNAR® and PREVNAR 13®) and *Neisseria meningitidis* (e.g., MENJUGATE®).

Upon the conjugation of a polysaccharide antigen to a carrier protein, the reaction mixture can be purified to remove free polysaccharide that has no protein conjugated thereto, free carrier protein that has no polysaccharide antigen conjugated thereto, and low molecular weight polysaccharide protein conjugates. Various methods for the purification of free polysaccharide, free protein, and low molecular weight conjugates are known in the art, including for example, hydrophobic chromatography, tangential ultrafiltration, diafiltration, etc. See, e.g., International Patent Application Publication No. WO00/38711, U.S. Pat. No. 6,146,902, and Lei et al., 2000, Dev. Biol. 103:259-264. Methods for reducing the amount of free polysaccharide further includes co-lyophilization of carrier protein and polysaccharide such as disclosed in U.S. Pat. No. 7,709,001 and U.S. Pub. Application No. 20110201791, which also showed that co-lyophilization of carrier protein and polysaccharide was preferred over discrete lyophilization of carrier protein and polysaccharide, particularly with respect to capsular polysaccharide 19A. However, co-lyophilization precludes the ability to optimize individual formulations and cycle parameters with less convenient handling and ability to produce carrier protein and polysaccharide serotype supplies with desired solution sizes.

Therefore, there is a continuing need for improved methods of producing stable polysaccharide protein conjugates that are free from impurities such as free polysaccharide and low molecular weight conjugates.

BRIEF SUMMARY OF THE INVENTION

The present invention provides a process for producing multivalent pneumococcal polysaccharide carrier protein conjugates for use in pneumococcal vaccines in which activated pneumococcal polysaccharides and carrier protein are discretely or separately lyophilized as lyospheres. The lyospheres may be mixed in predefined ratios, which are then reconstituted in an organic solvent to provide a reconstituted mixture of activated polysaccharide and carrier protein which are then conjugated together to produce the multivalent pneumococcal polysaccharide carrier protein conjugates for use in pneumococcal vaccines. The process of discrete drying of the polysaccharides and carrier protein into lyospheres provides various advantages over co-lyophilization of polysaccharides and carrier protein, including but not limited to, ability to optimize individual formulations and cycle parameters, convenient handling, and ability to produce individual polysaccharide and carrier protein preparations with a desired solution size.

The present invention provides a method for making a composition comprising *Streptococcus pneumoniae* polysaccharides from one *Streptococcus pneumoniae* serotype covalently linked to a carrier protein, the method comprising:

(a) providing a first lysophere composition comprising activated *Streptococcus pneumoniae* polysaccharides from a *Streptococcus pneumoniae* serotype and a second lysophere composition comprising carrier protein;

(b) combining an amount of the first lysophere composition and an amount of the second lysophere composition together to provide a lysophere mixture having a predetermined ratio of the activated polysaccharide to the carrier protein;

(c) reconstituting the lysophere mixture in an organic solvent and mixing to provide a reconstituted mixture; and (d) adding a reducing agent to the reconstituted mixture to produce a conjugate solution comprising a carrier protein conjugated to the polysaccharides of the one *Streptococcus pneumoniae* serotype.

In another embodiment, the present invention provides a method for making a composition comprising one or more *Streptococcus pneumoniae* polysaccharides covalently linked to a carrier protein, the method comprising:

(a) providing a first lysophere composition comprising one or more activated *Streptococcus pneumoniae* polysaccharides from a *Streptococcus pneumoniae* serotype and a second lysophere composition comprising carrier protein;

(b) combining an amount of the first lysophere composition and an amount of the second lysophere composition together to provide a lysophere mixture having a predetermined ratio of the one or more activated polysaccharide to the carrier protein;

(c) reconstituting the lysophere mixture in an organic solvent and mixing to provide a reconstituted mixture; and (d) adding a reducing agent to the reconstituted mixture to produce a conjugate solution comprising a carrier protein conjugated to the polysaccharides of the one or more *Streptococcus pneumoniae* serotype.

In another embodiment, the present invention provides a method for making a composition comprising two or more *Streptococcus pneumoniae* polysaccharides covalently linked to a carrier protein, the method comprising:

(a) providing a first lysophere composition comprising two or more activated *Streptococcus pneumoniae* polysaccharides from a *Streptococcus pneumoniae* serotype and a second lysophere composition comprising carrier protein;

(b) combining an amount of the first lysophere composition and an amount of the second lysophere composition together to provide a lysophere mixture having a predetermined ratio of the two or more activated polysaccharide to the carrier protein;

(c) reconstituting the lysophere mixture in an organic solvent and mixing to provide a reconstituted mixture; and (d) adding a reducing agent to the reconstituted mixture to produce a conjugate solution comprising a carrier protein conjugated to the polysaccharides of the two or more *Streptococcus pneumoniae* serotype.

In particular embodiments of any one of the methods of the invention, the first and second lysophere compositions are prepared by a sublimative drying process selected from lyophilization and radiant energy vacuum (REV) dehydration (microwave vacuum drying (MDV)).

In particular embodiments, each of the first and second lysophere compositions has a final moisture content of about 6% or less. In particular embodiments, each of the first and second lysophere compositions has a final moisture content of about 5% or less. In particular embodiments, each of the first and second lysophere compositions has a final moisture content of about 4% or less. In particular embodiments, each of the first and second lysophere compositions has a final moisture content of about 3% or less. In particular embodiments, each of the first and second lysophere compositions has a final moisture content of about 2% or less.

In particular embodiments, the first and second lysophere compositions are prepared by sublimative drying of a first aqueous solution comprising activated *Streptococcus pneumoniae* polysaccharides from one, two, or more *Streptococcus pneumoniae* serotypes and a second aqueous solution comprising a carrier protein and a buffer to produce the first and second dried compositions, wherein the first and second aqueous solutions comprise about 0.5% or more sucrose and wherein the sublimative drying is selected from lyophilization and radiant energy vacuum (REV) dehydration. In particular embodiments, the first aqueous solution comprises about 4% to 6% sucrose and the second aqueous solution comprises about 4% to 8% sucrose.

In particular embodiments, the first aqueous solution comprises the polysaccharide at a concentration of about 6 to 9 mg/mL and the second aqueous solution comprises the carrier protein at a concentration of about 6 to 12 mg/mL. In particular embodiments, the first aqueous solution comprises the polysaccharide at a concentration of about 6 or 9 mg/mL and the second aqueous solution comprises the carrier protein at a concentration of about 6, 9, or 12 mg/mL.

In particular embodiments, the organic solvent is an aprotic solvent. In particular embodiments, the aprotic solvent is dichloromethane, tetrahydrofuran, ethyl acetate acetonitrile, dimethylformamide, dimethylsulfoxide (DMSO), acetone, or hexamethylphosphoric triamde. In particular embodiments, the organic solvent is DMSO.

In particular embodiments of the method, the reconstituting in step (c) is performed in eight minutes or less. In particular embodiments, the reconstituting is performed in six minutes or less. In particular embodiments, the reconstituting is performed in four minutes or less. In particular embodiments, the reconstituting is performed in two minutes or less. In particular embodiments, the reconstituting is performed in about two minutes. In particular embodiments, the reconstituting is performed in one minute or less.

In particular embodiments, the mixing in step (c) is performed in 120 minutes or less. In particular embodiments, the mixing is performed in 90 minutes or less. In particular embodiments, the mixing is performed in 60 minutes or less. In particular embodiments, the mixing is performed in 30 minutes or less. In particular embodiments, the mixing is performed in 10 minutes or less.

In particular embodiments, the conjugate solution comprises polysaccharide conjugated to the carrier protein at a ratio from about 0.6 to about 1.3 polysaccharide to carrier protein on a weight to weight basis. In particular embodiments, the conjugate solution comprises polysaccharide conjugated to the carrier protein at a ratio from about 0.9 to about 1.5 polysaccharide to carrier protein on a weight to weight basis. In particular embodiments, the conjugate solution comprises polysaccharide conjugated to the carrier protein at a ratio from about 0.6 to about 1.5 polysaccharide to carrier protein on a weight to weight basis.

In particular embodiments, the conjugate solution comprises a free polysaccharide concentration that is less than about 15% of the total polysaccharide in the solution. In particular embodiments, the conjugate solution comprises a free polysaccharide concentration that is less than about 10% of the total polysaccharide in the solution.

In particular embodiments, the conjugate has a carrier protein lysine loss value of greater than five (mole/mole).

In particular embodiments, the conjugate solution comprises polysaccharide conjugated to the carrier protein at a ratio from about 0.6 to about 1.3 polysaccharide to carrier protein on a weight to weight basis, free polysaccharide concentration that is less than about 15% of the total polysaccharide in the solution, and the conjugate has a carrier protein lysine loss value of greater than five (mole/mole).

In particular embodiments, the buffer is a Histidine, Succinate, MES, MOPS, HEPES, or Acetate buffer in a pH range of 5.0-7.0.

In particular embodiments, the buffer is a Phosphate or a Citrate buffer in a pH range of 5.0-7.0.

In particular embodiments, the polysaccharides are obtained from a *Streptococcus pneumoniae* serotype selected from the group consisting of serotypes 1, 2, 3, 4, 5, 6A, 6B, 6C, 6D, 6E, 6G, 6H, 7F, 7A, 7B, 7C, 8, 9A, 9L, 9N, 9V, 10F, 10A, 10B, 10C, 11F, 11A, 11B, 11C, 11D, 11E, 12F, 12A, 12B, 13, 14, 15F, 15A, 15B, 15C, 16F, 16A, 17F, 17A, 18F, 18A, 18B, 18C, 19F, 19A, 19B, 19C, 20A, 20B, 21, 22F, 22A, 23F, 23A, 23B, 24F, 24A, 24B, 25F, 25A, 27, 28F, 28A, 29, 31, 32F, 32A, 33F, 33A, 33B, 33C, 33D, 33E, 34, 35F, 35A, 35B, 35C, 36, 37, 38, 39, 40, 41F, 41A, 42, 43, 44, 45, 46, 47F, 47A, 48, CWPS1, CWPS2, and CWPS3.

In particular embodiments, the *Streptococcus pneumoniae* polysaccharide is activated by reacting with an oxidizing agent.

In particular embodiments, the carrier protein is an inactivated bacterial toxoid selected from the group consisting of tetanus toxoid, diphtheria toxoid, pertussis toxoid, bacterial cytolysins or pneumolysin. In particular embodiments, the inactivated bacterial toxoid is $CRM_{197}$.

In particular embodiments, the conjugate solution is sterile filtered.

The present invention provides a method for making a composition comprising one or more *Streptococcus pneumoniae* polysaccharide covalently linked to a carrier protein, the method comprising
(a) providing (i) a first aqueous solution comprising activated *Streptococcus pneumoniae* polysaccharides from one or more *Streptococcus pneumoniae* serotypes and (ii) a second aqueous solution comprising a carrier protein and a buffer;
(b) separately drying the first aqueous solution and the second aqueous solution in a sublimative drying process for producing lyospheres to produce a first lyosphere composition comprising dried one or more activated polysaccharides and a second lyosphere composition comprising dried carrier protein;
(c) combining an amount of the first lyosphere composition and an amount of the second lysophere composition together to provide a lysophere mixture having a predetermined ratio of the one or more activated polysaccharide to the carrier protein;
(d) reconstituting the lyosphere mixture in an organic solvent and mixing to provide a reconstituted mixture; and
(e) adding a reducing agent to the reconstituted mixture to produce a conjugate solution comprising a carrier protein conjugated to the one or more activated polysaccharides of the *Streptococcus pneumoniae* serotype.

In particular embodiments of the method, the sublimative drying process selected from lyophilization and radiant energy vacuum (REV) dehydration.

In particular embodiments, each of the first and second lyosphere compositions has a final moisture content of about 6% or less. In particular embodiments, each of the first and second lyosphere compositions has a final moisture content of about 5% or less. In particular embodiments, each of the first and second lyosphere compositions has a final moisture content of about 4% or less. In particular embodiments, each of the first and second lyosphere compositions has a final moisture content of about 3% or less. In particular embodiments, each of the first and second lyosphere compositions has a final moisture content of about 2% or less.

In particular embodiments, the first and second aqueous solutions comprise about 0.5% or more sucrose. In particular embodiments, the first aqueous solution comprises about 4% to 6% sucrose and the second aqueous solution comprises about 4% to 8% sucrose.

In particular embodiments, the first aqueous solution comprises the polysaccharide at a concentration of about 6 to 9 mg/mL and the second aqueous solution comprises the carrier protein at a concentration of about 6 to 12 mg/mL. In particular embodiments, the first aqueous solution comprises the polysaccharide at a concentration of about 6 or 9 mg/mL and the second aqueous solution comprises the carrier protein at a concentration of about 6, 9, or 12 mg/mL.

In particular embodiments, the organic solvent is an aprotic solvent. In particular embodiments, the aprotic solvent is dichloromethane, tetrahydrofuran, ethyl acetate acetonitrile, dimethylformamide, acetone, dimethylsulfoxide (DMSO), or hexamethylphosphoric triamde. In particular embodiments, the organic solvent is DMSO.

In particular embodiments of the method, the reconstituting in step (d) is performed in eight minutes or less. In particular embodiments, the reconstituting is performed in six minutes or less. In particular embodiments, the reconstituting is performed in four minutes or less. In particular embodiments, the reconstituting is performed in two minutes or less. In particular embodiments, the reconstituting is performed in about two minutes. In particular embodiments, the reconstituting is performed in one minute or less.

In particular embodiments, the mixing in step (d) is performed in 120 minutes or less. In particular embodiments, the mixing is performed in 90 minutes or less. In particular embodiments, the mixing is performed in 60 minutes or less. In particular embodiments, the mixing is performed in 30 minutes or less. In particular embodiments, the mixing is performed in 10 minutes or less.

In particular embodiments, the conjugate solution comprises polysaccharide conjugated to the carrier protein at a ratio from about 0.6 to about 1.3 polysaccharide to carrier protein on a weight to weight basis. In particular embodiments, the conjugate solution comprises polysaccharide conjugated to the carrier protein at a ratio from about 0.9 to about 1.5 polysaccharide to carrier protein on a weight to weight basis. In particular embodiments, the conjugate solution comprises polysaccharide conjugated to the carrier protein at a ratio from about 0.6 to about 1.5 polysaccharide to carrier protein on a weight to weight basis.

In particular embodiments, the conjugate solution comprises a free polysaccharide concentration that is less than about 15% of the total polysaccharide in the solution. In particular embodiments, the conjugate solution comprises a free polysaccharide concentration that is less than about 10% of the total polysaccharide in the solution.

In particular embodiments, the conjugate has a carrier protein lysine loss value of greater than five (mole/mole).

In particular embodiments, each conjugate solution comprises polysaccharide conjugated to the carrier protein at a ratio from about 0.6 to about 1.3 polysaccharide to carrier protein on a weight to weight basis, free polysaccharide concentration that is less than about 15% of the total polysaccharide in the solution, and the conjugate has a carrier protein lysine loss value of greater than five (mole/mole).

In particular embodiments, the buffer is a Histidine, Succinate, MES, MOPS, HEPES, or Acetate buffer in a pH range of 5.0-7.0.

In particular embodiments, the buffer is a Phosphate or a Citrate buffer in a pH range of 5.0-7.0.

In particular embodiments, the one or more polysaccharides are obtained from a *Streptococcus pneumoniae* serotype selected from the group consisting of serotypes 1, 2, 3, 4, 5, 6A, 6B, 6C, 6D, 6E, 6G, 6H, 7F, 7A, 7B, 7C, 8, 9A, 9L, 9N, 9V, 10F, 10A, 10B, 10C, 11F, 11A, 11B, 11C, 11D, 11E, 12F, 12A, 12B, 13, 14, 15F, 15A, 15B, 15C, 16F, 16A, 17F, 17A, 18F, 18A, 18B, 18C, 19F, 19A, 19B, 19C, 20A, 20B, 21, 22F, 22A, 23F, 23A, 23B, 24F, 24A, 24B, 25F, 25A, 27, 28F, 28A, 29, 31, 32F, 32A, 33F, 33A, 33B, 33C, 33D, 33E, 34, 35F, 35A, 35B, 35C, 36, 37, 38, 39, 40, 41F, 41A, 42, 43, 44, 45, 46, 47F, 47A, 48, CWPS1, CWPS2, and CWPS3.

In particular embodiments, the *Streptococcus pneumoniae* polysaccharide is activated by reacting with an oxidizing agent.

In particular embodiments, the carrier protein is an inactivated bacterial toxoid selected from the group consisting of tetanus toxoid, diphtheria toxoid, pertussis toxoid, bacterial cytolysins or pneumolysin. In particular embodiments, the inactivated bacterial toxoid is $CRM_{197}$.

In particular embodiments, the conjugate solution is sterile filtered.

The present invention further provides a method for making a composition comprising two or more conjugates, each conjugate having *Streptococcus pneumoniae* polysaccharides from one or more serotypes covalently linked to a carrier protein, the method comprising:

(a) providing
  (i) two or more first aqueous solutions, each first aqueous solution comprising activated polysaccharides of a specific *Streptococcus pneumoniae* serotype, wherein the polysaccharides have been reacted with an oxidizing agent to provide the activated polysaccharides and wherein the two or more first aqueous solutions are not the same; or,
  (ii) two or more first aqueous solutions, each first aqueous solution comprising activated polysaccharides of two or more *Streptococcus pneumoniae* serotypes wherein the polysaccharides have been reacted with an oxidizing agent to provide the activated polysaccharide and wherein the two or more first aqueous solutions are not the same;
(b) providing two or more second aqueous solutions, each comprising a carrier protein and a buffer, wherein the quantity of two or more second aqueous solutions corresponds to at least the quantity of two or more first aqueous solutions;
(c) separately drying the two or more first aqueous solutions and the two or more second aqueous solutions in a sublimative drying process for producing lyospheres to produce two or more first lyosphere compositions, each comprising dried polysaccharides and two or more second lyosphere compositions, each comprising dried carrier protein;
(d) independently combining an amount of a first lyosphere composition and an amount of a second lyosphere composition to provide a plurality of lyosphere mixtures, each having a predetermined ratio of activated polysaccharide to carrier protein;
(e) reconstituting the plurality of lyosphere mixtures in an organic solvent and mixing to provide a plurality of reconstituted mixtures;
(f) adding a reducing agent to the plurality of reconstituted mixtures to produce a plurality conjugate solutions; and
(g) combining two or more of the plurality of conjugate solutions to produce the composition comprising two or more conjugates, each conjugate having *Streptococcus pneumoniae* polysaccharides from one or more serotypes covalently linked to a carrier protein.

In particular embodiments of the method, the sublimative drying process is selected from lyophilization and radiant energy vacuum (REV) dehydration.

In particular embodiments, each of the first and second lyosphere compositions has a final moisture content of about 6% or less. In particular embodiments, each of the first and second lyosphere compositions has a final moisture content of about 5% or less. In particular embodiments, each of the first and second lyosphere compositions has a final moisture content of about 4% or less. In particular embodiments, each of the first and second lyosphere compositions has a final moisture content of about 3% or less. In particular embodiments, each of the first and second lyosphere compositions has a final moisture content of about 2% or less.

In particular embodiments, the first and second aqueous solutions comprise about 0.5% or more sucrose. In particular embodiments, the first aqueous solution comprises about 4% to 6% sucrose and the second aqueous solution comprises about 4% to 8% sucrose.

In particular embodiments, the first aqueous solution comprises the polysaccharide at a concentration of about 6 to 9 mg/mL and the second aqueous solution comprises the carrier protein at a concentration of about 6 to 12 mg/mL. In particular embodiments, the second aqueous solution comprises the first aqueous solution comprises the polysaccharide at a concentration of about 6 or 9 mg/mL and the carrier protein at a concentration of about 6, 9, or 12 mg/mL.

In particular embodiments, the organic solvent is an aprotic solvent. In particular embodiments, the aprotic solvent is dichloromethane, tetrahydrofuran, ethyl acetate acetonitrile, dimethylformamide, acetone, dimethylsulfoxide (DMSO), or hexamethylphosphoric triamde. In particular embodiments, the organic solvent is DMSO.

In particular embodiments of the method, the reconstituting in step (e) is performed in eight minutes or less. In particular embodiments, the reconstituting is performed in six minutes or less. In particular embodiments, the reconstituting is performed in four minutes or less. In particular embodiments, the reconstituting is performed in two minutes or less. In particular embodiments, the reconstituting is performed in about two minutes. In particular embodiments, the reconstituting is performed in one minute or less.

In particular embodiments, the mixing in step (e) is performed in 120 minutes or less. In particular embodiments, the mixing is performed in 90 minutes or less. In particular embodiments, the mixing is performed in 60 minutes or less. In particular embodiments, the mixing is performed in 30 minutes or less. In particular embodiments, the mixing is performed in 10 minutes or less.

In particular embodiments, each conjugate solution comprises polysaccharide conjugated to the carrier protein at a ratio from about 0.6 to about 1.3 polysaccharide to carrier protein on a weight to weight basis. In particular embodiments, each conjugate solution comprises polysaccharide conjugated to the carrier protein at a ratio from about 0.9 to about 1.5 polysaccharide to carrier protein on a weight to weight basis. In particular embodiments, each conjugate solution comprises polysaccharide conjugated to the carrier protein at a ratio from about 0.6% to about 1.5 polysaccharide to carrier protein on a weight to weight basis.

In particular embodiments, the conjugate solution comprises a free polysaccharide concentration that is less than about 15% of the total polysaccharide in the solution. In particular embodiments, the conjugate solution comprises a free polysaccharide concentration that is less than about 10% of the total polysaccharide in the solution.

In particular embodiments, the conjugate has a carrier protein lysine loss value of greater than five (mole/mole).

In particular embodiments, each conjugate solution comprises polysaccharide conjugated to the carrier protein at a ratio from about 0.6 to about 1.3 polysaccharide to carrier protein on a weight to weight basis, free polysaccharide concentration that is less than about 15% of the total polysaccharide in the solution, and the conjugate has a carrier protein lysine loss value of greater than five (mole/mole).

In particular embodiments, the buffer is a Histidine, Succinate, MES, MOPS, HEPES, or Acetate buffer in a pH range of 5.0-7.0.

In particular embodiments, the buffer is a Phosphate or a Citrate buffer in a pH range of 5.0-7.0.

In particular embodiments, the polysaccharides are obtained from a *Streptococcus pneumoniae* serotype selected from the group consisting of serotypes 1, 2, 3, 4, 5, 6A, 6B, 6C, 6D, 6E, 6G, 6H, 7F, 7A, 7B, 7C, 8, 9A, 9L, 9N, 9V, 10F, 10A, 10B, 10C, 11F, 11A, 11B, 11C, 11D, 11E, 12F, 12A, 12B, 13, 14, 15F, 15A, 15B, 15C, 16F, 16A, 17F, 17A, 18F, 18A, 18B, 18C, 19F, 19A, 19B, 19C, 20A, 20B, 21, 22F, 22A, 23F, 23A, 23B, 24F, 24A, 24B, 25F, 25A, 27, 28F, 28A, 29, 31, 32F, 32A, 33F, 33A, 33B, 33C, 33D, 33E, 34, 35F, 35A, 35B, 35C, 36, 37, 38, 39, 40, 41F, 41A, 42, 43, 44, 45, 46, 47F, 47A, 48, CWPS1, CWPS2, and CWPS3.

In particular embodiments, the *Streptococcus pneumoniae* polysaccharide is activated by reacting with an oxidizing agent.

In particular embodiments, the carrier protein is an inactivated bacterial toxoid selected from the group consisting of tetanus toxoid, diphtheria toxoid, pertussis toxoid, bacterial cytolysins or pneumolysin. In particular embodiments, the inactivated bacterial toxoid is $CRM_{197}$.

In particular embodiments, the conjugate solution is sterile filtered.

The present invention further comprises a method for making a multivalent pneumococcal conjugate vaccine containing *Streptococcus pneumoniae* serotype polysaccharides 1, 2, 3, 4, 5, 6B, 7F, 8, 9N, 9V, 10A, 11A, 12F, 14, 15B, 17F, 18C, 19A, 19F, 20, 22F, 23F, and 33F conjugated to carrier proteins, the method comprising:
  (a) providing 23 carrier protein lyosphere compositions and 23 activated polysaccharide lyosphere compositions, each comprising dried activated polysaccharides from a *Streptococcus pneumoniae* serotype selected from 1, 2, 3, 4, 5, 6B, 7F, 8, 9N, 9V, 10A, 11A, 12F, 14, 15B, 17F, 18C, 19A, 19F, 20, 22F, 23F, and 33F, wherein none of the 23 activated polysaccharide lyosphere compositions comprises activated polysaccharides from the same *Streptococcus pneumoniae* serotype;
  (b) separately combining each of the 23 carrier protein lyosphere compositions and each of the 23 activated polysaccharide lyosphere compositions to provide 23 lyosphere mixtures, each having a predetermined ratio of activated polysaccharide to carrier protein, wherein none of the 23 lyosphere mixtures comprise activated polysaccharides from the same *Streptococcus pneumoniae* serotype;
  (c) separately reconstituting each of the 23 lyospheres mixtures with an organic solvent and mixing to produce a plurality of reconstituted mixtures, wherein none of the 23 reconstituted mixtures comprises activated polysaccharides from the same *Streptococcus pneumoniae* serotype;
  (d) adding a reducing agent to each of the 23 reconstituted mixtures to produce 23 conjugate solutions, each comprising a carrier protein conjugated to polysaccharides of a specific *Streptococcus pneumoniae* serotype, wherein none of the 23 conjugate solutions comprise activated polysaccharides from the same *Streptococcus pneumoniae* serotype; and
  (e) combining the 23 conjugate solutions to provide the multivalent immunogenic complex or vaccine against *Streptococcus pneumoniae* serotype polysaccharides 1, 2, 3, 4, 5, 6B, 7F, 8, 9N, 9V, 10A, 11A, 12F, 14, 15B, 17F, 18C, 19A, 19F, 20, 22F, 23F, and 33F.

The present invention further comprises a method for making a multivalent immunogenic complex or vaccine against *Streptococcus pneumoniae* serotype polysaccharides 1, 3, 4, 5, 6A, 6B, 7F, 9V, 14, 18C, 19A, 19F, 22F, 23F, and 33F, the method comprising:
  (a) providing 15 carrier protein lyosphere compositions and 15 activated polysaccharide lyosphere compositions, each comprising dried activated polysaccharides from a *Streptococcus pneumoniae* serotype selected from 1, 3, 4, 5, 6A, 6B, 7F, 9V, 14, 18C, 19A, 19F, 22F, 23F, and 33F, wherein none of the 15 activated polysaccharide lyosphere compositions comprises activated polysaccharides from the same *Streptococcus pneumoniae* serotype;
  (b) separately combining each of the 15 carrier protein lyosphere compositions and each of the 15 activated polysaccharide lyosphere compositions to provide 15 lyosphere mixtures, each having a predetermined ratio of activated polysaccharide to carrier protein, wherein none of the 15 lyosphere mixtures comprise activated polysaccharides from the same *Streptococcus pneumoniae* serotype;
  (c) separately reconstituting each of the 15 lyospheres mixtures with an organic solvent and mixing to produce a plurality of reconstituted mixtures, wherein none of the 15 reconstituted mixtures comprises activated polysaccharides from the same *Streptococcus pneumoniae* serotype;
  (d) adding a reducing agent to each of the 15 reconstituted mixtures to produce 15 conjugate solutions, each comprising a carrier protein conjugated to polysaccharides of a specific *Streptococcus pneumoniae* serotype, wherein none of the 15 conjugate solutions comprise activated polysaccharides from the same *Streptococcus pneumoniae* serotype; and
  (e) combining the 15 conjugate solutions to provide the multivalent pneumococcal conjugate vaccine containing *Streptococcus pneumoniae* serotype polysaccharides 1, 3, 4, 5, 6A, 6B, 7F, 9V, 14, 18C, 19A, 19F, 22F, 23F, and 33F conjugated to carrier proteins.

The present invention further provides a method for making a multivalent pneumococcal conjugate vaccine containing *Streptococcus pneumoniae* serotype polysaccharides 1, 3, 4, 5, 6A, 6B, 7F, 9V, 14, 18C, 19A, 19F, and 23F conjugated to carrier proteins, the method comprising:
  (a) providing 13 carrier protein lyosphere compositions and 13 activated polysaccharide lyosphere compositions, each comprising dried activated polysaccharides from a *Streptococcus pneumoniae* serotype selected from 1, 3, 4, 5, 6A, 6B, 7F, 9V, 14, 18C, 19A, 19F, and 23F, wherein none of the 13 activated polysaccharide lyosphere compositions comprises activated polysaccharides from the same *Streptococcus pneumoniae* serotype;
  (b) separately combining each of the 13 carrier protein lyosphere compositions and each of the 13 activated polysaccharide lyosphere compositions to provide 13 lyosphere mixtures, each having a predetermined ratio of activated polysaccharide to carrier protein, wherein none of the 13 lyosphere mixtures comprise activated polysaccharides from the same *Streptococcus pneumoniae* serotype;

(c) separately reconstituting each of the 13 lyospheres mixtures with an organic solvent and mixing to produce a plurality of reconstituted mixtures, wherein none of the 13 reconstituted mixtures comprises activated polysaccharides from the same *Streptococcus pneumoniae* serotype;

(d) adding a reducing agent to each of the 13 reconstituted mixtures to produce 13 conjugate solutions, each comprising a carrier protein conjugated to polysaccharides of a specific *Streptococcus pneumoniae* serotype, wherein none of the 13 conjugate solutions comprise activated polysaccharides from the same *Streptococcus pneumoniae* serotype; and (e) combining the 13 conjugate solutions to provide the multivalent pneumococcal conjugate vaccine containing *Streptococcus pneumoniae* serotype polysaccharides 1, 3, 4, 5, 6A, 6B, 7F, 9V, 14, 18C, 19A, 19F, and 23F conjugated to carrier proteins.

The present invention further provides a method for making a multivalent pneumococcal conjugate vaccine containing *Streptococcus pneumoniae* serotype polysaccharides 1, 4, 5, 6B, 7F, 9V, 14, 18C, 19F, and 23F conjugated to carrier proteins, the method comprising:

(a) providing 10 carrier protein lyosphere compositions and 10 activated polysaccharide lyosphere compositions, each comprising dried activated polysaccharides from a *Streptococcus pneumoniae* serotype selected from 1, 4, 5, 6B, 7F, 9V, 14, 18C, 19F, and 23F, wherein none of the 10 activated polysaccharide lyosphere compositions comprises activated polysaccharides from the same *Streptococcus pneumoniae* serotype;

(b) separately combining each of the 10 carrier protein lyosphere compositions and each of the 10 activated polysaccharide lyosphere compositions to provide 10 lyosphere mixtures, each having a predetermined ratio of activated polysaccharide to carrier protein, wherein none of the 10 lyosphere mixtures comprise activated polysaccharides from the same *Streptococcus pneumoniae* serotype;

(c) separately reconstituting each of the 10 lyospheres mixtures with an organic solvent and mixing to produce a plurality of reconstituted mixtures, wherein none of the 10 reconstituted mixtures comprises activated polysaccharides from the same *Streptococcus pneumoniae* serotype;

(d) adding a reducing agent to each of the 10 reconstituted mixtures to produce 10 conjugate solutions, each comprising a carrier protein conjugated to polysaccharides of a specific *Streptococcus pneumoniae* serotype, wherein none of the 10 conjugate solutions comprise activated polysaccharides from the same *Streptococcus pneumoniae* serotype; and (e) combining the 10 conjugate solutions to provide the multivalent pneumococcal conjugate vaccine containing *Streptococcus pneumoniae* serotype polysaccharides 1, 4, 5, 6B, 7F, 9V, 14, 18C, 19F, and 23F conjugated to carrier proteins.

In particular embodiments, each of the first and second lyosphere compositions has a final moisture content of about 6% or less. In particular embodiments, each of the first and second lyosphere compositions has a final moisture content of about 5% or less. In particular embodiments, each of the first and second lyosphere compositions has a final moisture content of about 4% or less. In particular embodiments, each of the first and second lyosphere compositions has a final moisture content of about 3% or less. In particular embodiments, each of the first and second lyosphere compositions has a final moisture content of about 2% or less.

In particular embodiments of the method, the sublimative drying process comprises separately freezing each aqueous solution comprising the carrier protein and each aqueous solution comprising the polysaccharides in the form of lyosphere beads.

In particular embodiments, the lyosphere carrier protein and lyosphere polysaccharide compositions are prepared by a sublimative drying of a plurality of separate aqueous polysaccharide solutions, each aqueous polysaccharide solution comprising activated *Streptococcus pneumoniae* polysaccharides from a particular enumerated *Streptococcus pneumoniae* serotypes as recited above, and a multiplicity of aqueous carrier protein solutions, each carrier protein solution comprising a carrier protein and a buffer to produce the dried polysaccharide and carrier protein compositions, wherein the number of aqueous carrier protein solutions correspond to at least the number of aqueous polysaccharide solutions, and wherein the aqueous polysaccharide and carrier protein solutions each comprise about 0.5% or more sucrose and wherein the sublimative drying is selected from lyophilization and radiant energy vacuum (REV) dehydration. In particular embodiments, the aqueous polysaccharide solutions each comprise about 4% to 6% sucrose and the aqueous carrier protein solutions each comprise about 4% to 8% sucrose.

In particular embodiments, the aqueous polysaccharide solutions each comprise the polysaccharide at a concentration of about 6 to 9 mg/mL and the aqueous carrier protein solutions each comprise the carrier protein at a concentration of about 6 to 12 mg/mL. In particular embodiments, the aqueous polysaccharide solutions each comprise the polysaccharide at a concentration of about 6 or 9 mg/mL and the aqueous carrier protein solutions each comprise carrier protein at a concentration of about 6, 9, or 12 mg/mL.

In particular embodiments, the organic solvent is an aprotic solvent. In particular embodiments, the aprotic solvent is dichloromethane, tetrahydrofuran, ethyl acetate acetonitrile, dimethylformamide, dimethylsulfoxide (DMSO), acetone, or hexamethylphosphoric triamde.

In particular embodiments, the organic solvent is DMSO.

In particular embodiments of the method, the reconstituting in step (c) is performed in eight minutes or less. In particular embodiments, the reconstituting is performed in six minutes or less. In particular embodiments, the reconstituting is performed in four minutes or less. In particular embodiments, the reconstituting is performed in two minutes or less. In particular embodiments, the reconstituting is performed in about two minutes. In particular embodiments, the reconstituting is performed in one minute or less.

In particular embodiments, the mixing in step (c) is performed in 120 minutes or less. In particular embodiments, the mixing is performed in 90 minutes or less. In particular embodiments, the mixing is performed in 60 minutes or less. In particular embodiments, the mixing is performed in 30 minutes or less. In particular embodiments, the mixing is performed in 10 minutes or less.

In particular embodiments, each conjugate solution comprises polysaccharide conjugated to the carrier protein at a ratio from about 0.6 to about 1.3 polysaccharide to carrier protein on a weight to weight basis. In particular embodiments, each conjugate solution comprises polysaccharide conjugated to the carrier protein at a ratio from about 0.9 to about 1.5 polysaccharide to carrier protein on a weight to weight basis. In particular embodiments, each conjugate solution comprises polysaccharide conjugated to the carrier protein at a ratio from about 0.6 to about 1.5 polysaccharide to carrier protein on a weight to weight basis.

In particular embodiments, the conjugate solutions comprise a free polysaccharide concentration that is less than about 15% of the total polysaccharide in the solution. In particular embodiments, the conjugate solutions comprise a free polysaccharide concentration that is less than about 10% of the total polysaccharide in the solution.

In particular embodiments, the conjugate has a carrier protein lysine loss value of greater than five (mole/mole).

In particular embodiments, each conjugate solution comprises polysaccharide conjugated to the carrier protein at a ratio from about 0.6 to about 1.3 polysaccharide to carrier protein on a weight to weight basis, free polysaccharide concentration that is less than about 15% of the total polysaccharide in the solution, and the conjugate has a carrier protein lysine loss value of greater than five (mole/mole).

In particular embodiments, the carrier protein is an inactivated bacterial toxoid selected from the group consisting of tetanus toxoid, diphtheria toxoid, pertussis toxoid, bacterial cytolysins or pneumolysin. In particular embodiments, the inactivated bacterial toxoid is $CRM_{197}$.

In particular embodiments, the *Streptococcus pneumoniae* polysaccharide is activated by reacting with an oxidizing agent.

In particular embodiments, the conjugate solution is sterile filtered.

DETAILED DESCRIPTION OF THE INVENTION

I. Definitions

As used herein, the term "polysaccharide" (Ps) is meant to include any antigenic saccharide element (or antigenic unit) commonly used in the immunologic and bacterial vaccine arts, including, but not limited to, a "saccharide", an "oligosaccharide", a "polysaccharide", a "liposaccharide", a "lipo-oligosaccharide (LOS)", a "lipopolysaccharide (LPS) ", a "glycosylate", a "glycoconjugate" and the like. Depending on the context, Ps may singular or plural.

As used herein, the term "comprises" when used with the immunogenic composition of the invention refers to the inclusion of any other components (subject to limitations of "consisting of" language for the antigen mixture), such as adjuvants and excipients. The term "consisting of" when used with the multivalent polysaccharide-protein conjugate mixture refers to a mixture having those particular *S. pneumoniae* polysaccharide protein conjugates and no other *S. pneumoniae* polysaccharide protein conjugates from a different serotype.

As used herein, the term "reconstituting" or "reconstitution" refers to adding a liquid to a dried material to dissolve the dried material to provide a solution of the material dissolved therein. However, the solution provided by the reconstitution may have concentration gradients or layers of the dissolved material therein. Therefore, following reconstitution, the solution is physically agitated to provide a homogenous solution of the reconstituted material.

As used herein, the term "mixing" is use to refer to the physical agitation of a solution by shaking, stirring, rocking, rotating, or the like.

As used herein, the term "homogenous solution" refers to a solution in which all components are thoroughly mixed such there are no concentration gradients or layers between the components in the solution.

As defined herein, the terms "precipitation", "precipitate", "particulate formation", "clouding", and "aggregation" may be used interchangeably and are meant to refer to any physical interaction or chemical reaction which results in the agglomeration of a polysaccharide-protein conjugate. The process of aggregation (e.g., protein aggregation) may be induced by numerous physicochemical stresses, including heat, pressure, pH, agitation, shear forces, freeze-thawing, dehydration, heavy metals, phenolic compounds, silicon oil, denaturants and the like.

As used herein, a "lyosphere" is a discrete particle of lyophilized material, for example, taking the form of a bead or sphere or other shape. A lyosphere may also be referred to as a lyoparticle sphereon, or lyobead. In some embodiments, the lyosphere diameter is from about 2 to about 12 mm, preferably from 2 to 8 mm, such as from 2.5 to 6 mm or 2.5 to 5 mm. In some embodiments, the volume of the lyosphere is from about 20 to 550 µL, preferably from 20 to 100 µL, such as from 20 to 50 µL. In embodiments wherein the lyosphere is not substantially spherical, the size of the lyosphere can be described with respect to its aspect ratio, which is the ratio of the longer dimension to the shorter dimension. The aspect ratio of the lyospheres can be from 0.5 to 2.5, preferably from 0.75 to 2, such as from 1 to 1.5.

As used herein, an "immunogenic composition" may be a multivalent composition containing one or more antigens conjugated to one or more carrier proteins. In certain embodiments of the invention, the antigen is a saccharide from an encapsulated bacteria. In such compositions, the saccharides are composed of long chains of sugar molecules that resemble the surface of certain types of bacteria. Encapsulated bacteria include, but are not limited to, *Streptococcus pneumoniae, Neisseria meningitides* and *Haemophilus influenzae* type b. The antigens may be from the same organism or may be from different organisms. In preferred embodiments of the invention, the antigens are *Streptococcus pneumoniae* capsular polysaccharides.

As used herein, the term "radiant energy vacuum (REV) dehydration" also refers to microwave vacuum drying (MVD).

II. The Process

The present invention provides a method or process for producing multivalent pneumococcal polysaccharide-protein conjugates that may be used as anti-pneumococcal vaccines, in which discrete (or separate) lyophilization of pneumococcal polysaccharides and carrier protein using various sublimative processes is followed by mixing the discretely lyophilized polysaccharides and carrier proteins under conditions that result in formation of a conjugate composition having low levels of free polysaccharide (e.g., less than 15% free polysaccharide).

The present invention is an improvement over prior art methods for producing multivalent pneumococcal polysaccharide-protein conjugates having a low level of free polysaccharide. Prior art methods such as those disclosed in U.S. Pat. No. 7,709,001 and U.S. Pub. Application No. 20110201791 use co-lyophilization of carrier protein and polysaccharide because co-lyophilization of the polysaccharide and carrier protein together was shown to result in a conjugate composition having low free polysaccharides (less than 18%) whereas a conjugate composition formulated by combining discretely lyophilized polysaccharide and carrier protein result in a composition having about 31% free polysaccharide as illustrated by the results shown in Table 1 of U.S. Pub. Application No. 20110201791.

TABLE 1*

Comparisons of Key Conjugate Characteristics for Serotype 19A Co-Lyophilization in DMSO vs. Discrete Lyophilization

| Characteristic | Co-Lyophilization (n = 6) | | Discrete Lyophilization (n = 6) | |
|---|---|---|---|---|
| | Mean | Standard Deviation | Mean | Standard Deviation |
| %0.3 Kd (CL-4B) polysaccharide | 67 | 7.2 | 58 | 13.0 |
| Free polysaccharide (%) | <18 | <3.5 | 31 | 9.2 |

*Results shown are shown are from Table 7 of U.S. Pub. Application No. 20110201791

However, the inventors of the present invention have discovered that under certain conditions, separately (or discretely) lyophilized carrier protein and activated polysaccharide may be conjugated to produce compositions comprising high molecular weight conjugates but unlike in U.S. Pub. Application Ser. No. 20110201791, the compositions have low levels of free polysaccharides. These certain conditions include combining a predetermined amount carrier protein lyospheres and a predetermined amount of a polysaccharide lyospheres together to form lyosphere mixtures and reconstituting the lyosphere mixtures in an organic solvent and mixing to provide conjugate solutions. In particular embodiments the organic solvent is dimethylsulfoxide (DMSO). Reconstituting these lyosphere mixtures instead of separately reconstituting carrier protein and polysaccharide lyospheres substantially reduces or eliminates the concentration gradient that typically occurs when two solutions are combined by adding one solution to the other solution or dissolving dried material into a solution. The reduction or elimination of the concentration gradient increases the yield of a composition comprising high molecular weight conjugates and low amounts of free polysaccharides (e.g., 15% or less free polysaccharide). The present invention provides various advantages over co-lyophilization of polysaccharides and carrier protein in a single composition, including but not limited to, ability to optimize individual formulations and cycle parameters, convenient handling, and ability to produce individual polysaccharide and carrier protein preparations with a desired solution size.

Figure 1:
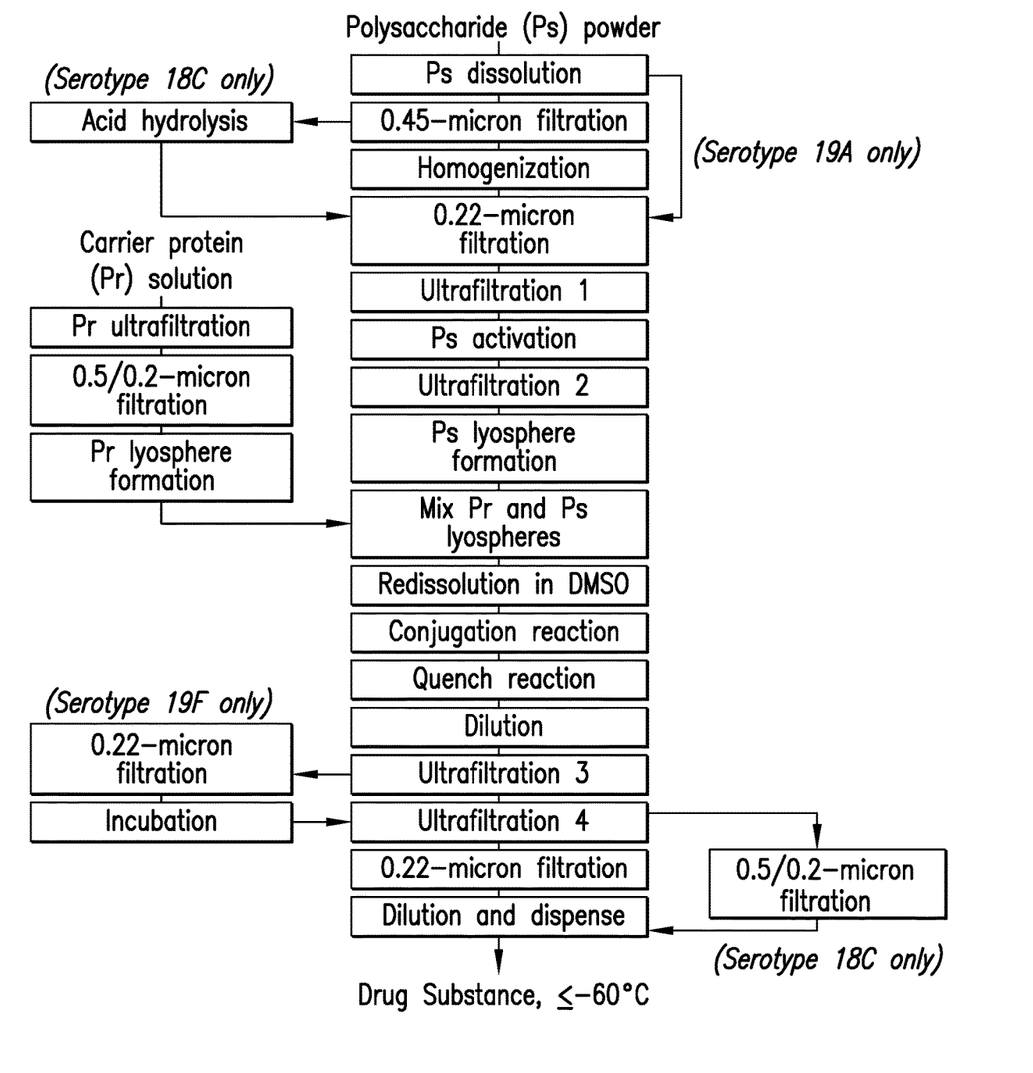
FIG. 1 shows a general scheme for making carrier protein (Pr) polysaccharide (Ps) conjugates.

FIG. 1 shows a general scheme for making carrier protein polysaccharide conjugates in which the carrier protein and polysaccharides are mixed as dried lyospheres as taught herein.

In general, purified pneumococcal capsular polysaccharide (Ps) powder is separately dissolved in water, and all serotypes, except serotype 19A, are 0.45-micron filtered. All serotypes, except serotype 19A, are homogenized to reduce the molecular mass of the Ps. Serotype 18C is size-reduced by acid hydrolysis at 90° C. or more. Serotype 19A is not size reduced due to its relatively low starting size. Homogenization pressure and number of passes through the homogenizer are controlled to serotype-specific targets to achieve a serotype-specific molecular mass. The polysaccharides are each 0.22-micron filtered and then concentrated and diafiltered against water in Ultrafiltration Step 1 using a 10 kD ultrafiltration membrane with open channel (type 5) to produce diafiltrate 1.

Diafiltrate 1 may then be adjusted to a serotype-specific temperature (between 4-22° C.) and pH (4-5) with sodium acetate buffer to minimize polysaccharide size reduction during the activation step. Polysaccharide activation is performed via periodate oxidation. For serotype 4, prior to activation, the solution is incubated at approximately 50° C. and pH 4 to partially deketalize the polysaccharide. Polysaccharide activation is initiated with the addition of a sodium metaperiodate solution. The amount of sodium metaperiodate added is serotype-specific, ranging from approximately 0.1 to 0.5 moles of sodium metaperiodate per mole of polysaccharide repeating unit. The serotype-specific charge of sodium metaperiodate is selected to achieve a target level of polysaccharide activation (moles aldehyde per mole of polysaccharide repeating unit).

In Ultrafiltration Step 2, for all serotypes the activated polysaccharide may be diafiltered and then concentrated by tangential flow ultrafiltration using a 10 kD ultrafiltration membrane with open channel to produce diafiltrate 2. At the end of the diafiltration, the diafiltrate 2 may be concentrated to a target of 15 g Ps/L. Preferably, the ultrafiltration for all serotypes is conducted at 2-8° C.

Diafiltrate 2 is then diluted in water with sucrose added to make a final concentration of about 4 to 12 mg/mL polysaccharide and 0.5% to 6% (V/V) sucrose and sublimatively dried in a process for producing lyospheres to produce lyospheres of dried polysaccharide having a final moisture content of 6% or less. The amount of sucrose that is added to the solution prior to lyophilization is serotype specific. In particular embodiments, two or more polysaccharides may be dried together to produce a dried polysaccharide mixture.

Purified carrier protein is diafiltered against 2 mM phosphate, pH 7.0 buffer using a 5 kDa tangential flow ultrafiltration membrane and then filtered through a 0.22-micron filter. The filtered solution is diluted in water with sucrose for a final concentration of about 6 to 12 mg/mL carrier protein and 4 to 10% (v/v) sucrose and sublimatively dried in a process for producing lyospheres to produce lyospheres of dried carrier protein having a final moisture content of 6% or less. Sublimative drying process for producing the lyospheres may include lyophilization or radiant energy vacuum (REV) dehydration.

In particular embodiments, the lyospheres have final moisture contents of about 5% or less. In particular embodiments, the lyospheres have final moisture contents of about 4% or less. In particular embodiments, the lyospheres have final moisture contents of about 3% or less. In particular embodiments, lyospheres have final moisture contents of about 2% or less.

The dried polysaccharide lyospheres and dried polysaccharide lyospheres are combined to provide a lyosphere mixture comprising polysaccharide lyospheres and carrier protein lyospheres. The polysaccharide lyospheres and carrier protein lyospheres are combined targeting a serotype-specific final polysaccharide concentration and polysaccharide:carrier protein ratio. In general, the carrier protein and polysaccharide are mixed in amounts that will provide a final conjugated polysaccharide:carrier protein ratio from about 0.6 to 1.3 (w/w).

The lyosphere mixture is reconstituted or redissolved in an organic solvent, for example, dimethylsulfoxide (DMSO) to provide a reconstituted mixture. In a preferred embodiment, the organic solvent is anhydrous and in particular embodiments, the anhydrous organic solvent is anhydrous DMSO.

In particular embodiments, following reconstitution, the reconstituted mixtures may be mixed for up to 30 minutes to provide a homogenous solution of the carrier protein and a homogenous solution of the polysaccharide. However, in particular embodiments, the mixing may occur over time period of 120 minutes or less, 90 minutes or less, 60 minutes or less, 30 minutes or less, or 10 minutes or less. In particular embodiments, 500 mM sodium phosphate, pH 7.2, buffer is added to the reconstituted mixture for a final concentration of 1.0 mM sodium phosphate.

To effect the conjugation reaction, a solution of sodium cyanoborohydride in water is prepared and 1.0 meq of sodium cyanoborohydride (1.0 mole of sodium cyanoborohydride per mole of polysaccharide repeating unit) is added to the reconstituted mixture to provide a conjugation solution. The molarity of the sodium cyanoborohydride solution is based on a target amount of about 0.5% total water content of the solution during conjugation. The conjugation solution is allowed to react at serotype-specific temperature for a serotype-specific duration to produce a carrier protein:polysaccharide conjugate intermediate.

Next, a solution of sodium borohydride in water is prepared and 2.0 meq of sodium borohydride (relative to polysaccharide repeating units) is added to the conjugation solution. The molarity of the sodium borohydride solution is based on a target amount of about 1.0% total water content in the conjugation solution after borohydride addition. The conjugation solution is allowed to react for three hours (except for certain serotypes such as serotype 7F, which is allowed to react for two hours) at ambient temperature to produce the carrier protein:polysaccharide conjugate.

To quench the conjugation reaction, the conjugation solution is diluted in a dilution step to 20% (v/v) or less organic solvent by slowly adding the conjugation solution to a solution of 150 mM sodium chloride (150 mM sodium chloride with 0.025% (w/v) polysorbate 20 for conjugates comprising polysaccharides from particular serotypes to produce a quenched conjugate solution. In particular embodiments the temperature is maintained at 15° C. or less during the dilution step. After about an hour, 1.5 M potassium phosphate, pH 6.0, is added to the solution to a final concentration of 25 mM potassium phosphate. Conjugation performance may be assessed by overall polysaccharide and carrier protein consumption, conjugate polysaccharide to carrier protein ratio, and conjugate molecular weight.

In Ultrafiltration Step 3, the quenched conjugate solution may be concentrated to about 2.5 g/L and diafiltered against up to about 10 diavolumes of 150 mM sodium chloride or 25 mM potassium phosphate in 150 mM sodium chloride at 2-8° C. using a 30 kDa tangential flow ultrafiltration membrane to produce diafiltrate 3. The polysaccharide concentration in diafiltrate 3 from ultrafiltration step 3 may be determined by high performance size exclusion chromatography (HPSEC) ultraviolet multi-angle light scattering refractive index (UV-MALS-RI). For conjugates comprising polysaccharides from some serotypes such as serotype 19F, diafiltrate 3 may be filtered through a 0.22-micron filter to produce a filtrate that is subsequently incubated at 22° C. for about 120 hours.

In Ultrafiltration Step 4, diafiltrate 3 or filtrate from Ultrafiltration Step 3 may be concentrated to a polysaccharide concentration of about 2.5 g/L and diafiltered against 20 diavolumes of 10 mM L-histidine in 150 mM sodium chloride, pH 7.0 at 2-8° C. using a 300 kDa tangential flow ultrafiltration membrane to produce diafiltrate 4. For conjugates comprising polysaccharides from certain serotypes, e.g., serotype 7F, the conjugate may be diafiltered against a 100 kDa tangential flow ultrafiltration membrane; e.g., conjugates comprising serotype 6A, 6B, and 18C polysaccharides, may be concentrated to about 3.5 g/L and diafiltered against a buffer comprising 150 mM sodium chloride and 0.03% (w/v) polysorbate 20, pH 7.0, at 2-8° C. using a 300 kDa tangential flow ultrafiltration membrane to produce diafiltrate 4. Conjugates comprising serotype 7F, 19A, 19F and 23F polysaccharides may be concentrated to about 2.0 g/L and diafiltered against a buffer comprising 150 mM sodium chloride and 0.015% (w/v) polysorbate 20, pH 7.0, at 2-8° C. using a 300 kDa regenerated cellulose tangential flow ultrafiltration membrane to produce diafiltrate 4. The polysaccharide concentration in diafiltrate 2 may be determined by HPSEC UV-MALS-RI. The buffer may be 10-50 mM acetate, phosphate, TRIS, HEPES, or an amino acid buffer such as a histidine. In particular embodiments, the buffer is 10 mM L-histidine.

Diafiltrate 4 from Ultrafiltration Step 4 may be filtered through a 0.22-micron filter to produce a second filtrate. The polysaccharide concentration of the second filtrate may be determined by HPSEC UV-MALS-RI. If the polysaccharide concentration of the second filtrate is greater than 1.0 g/L, the second filtrate may be diluted to a polysaccharide concentration of 1.0 g/L with additional 10 mM L-histidine in 150 mM sodium chloride, pH 7.0. This provides a Monovalent Bulk Conjugate intermediate (MBC) or monovalent drug substance. The MBC may be dispensed into aliquots and frozen at −60° C. to −80° C.

Diafiltrate 4 from Ultrafiltration Step 4 for conjugates comprising serotype 6A, 6B, and 18C polysaccharides may be filtered through a dual-membrane 0.5/0.2-micron filter to produce a second filtrate. The polysaccharide concentration of the second filtrate may be determined by HPSEC UV-MALS-RI. If the polysaccharide concentration of the second filtrate is greater than 1.0 g/L, the second filtrate may be diluted to a polysaccharide concentration of 1.0 g/L with additional 10 mM L-histidine in 150 mM sodium chloride, 0.03% (w/v) polysorbate 20, pH 7.0. This provides an MBC or monovalent drug substance. The MBC may be dispensed into aliquots and frozen at −60° C. to −80° C.

Diafiltrate 4 for conjugates comprising serotype 7F, 19A, 19F, and 23F polysaccharides may be filtered through a 0.22-micron filter to produce a second filtrate. The polysaccharide concentration of the second filtrate may be determined by HPSEC UV-MALS-RI. If the polysaccharide concentration of the second filtrate is greater than 1.0 g/L, the second filtrate may be diluted to a polysaccharide concentration of 1.0 g/L with additional 10 mM L-histidine in 150 mM sodium chloride, 0.015% (w/v) polysorbate 20, pH 7.0. This provides an MBC or monovalent drug substance. The MBC may be dispensed into aliquots and frozen at −60° C. to −80° C.

III. Polysaccharides

Capsular polysaccharides from *Steptococcus pneumoniae* can be prepared by standard techniques known to those skilled in the art. For example, polysaccharides can be isolated from bacteria and may be sized to some degree by known methods (see, e.g., European Patent Nos. EP497524 and EP497525); and in particular embodiments, by microfluidisation accomplished using a homogenizer or by chemical hydrolysis. In one embodiment, *S. pneumoniae* strains corresponding to each polysaccharide serotype are grown in a soy-based medium. The individual polysaccharides are then purified through standard steps including centrifugation, precipitation, and ultra-filtration. See, e.g., U.S. Patent Application Publication No. 2008/0286838 and U.S. Pat. No. 5,847,112. Polysaccharides can be sized in order to reduce viscosity and/or to improve filterability of subsequent conjugated products. In the present invention, capsular polysaccharides are prepared from one or more of serotypes 1, 2, 3, 4, 5, 6A, 6B, 6C, 6D, 7B, 7C, 7F, 8, 9N, 9V, 10A, 11A, 12F, 14, 15A, 15B, 15C, 16F, 17F, 18C, 19A, 19F, 20, 21, 22A, 22F, 23A, 23B, 23F, 24F, 27, 28A, 31, 33F, 34, 35A, 35B, 35F, and 38.

IV. Carrier Proteins

In a particular embodiment of the present invention, $CRM_{197}$ is used as the carrier protein. $CRM_{197}$ is a non-toxic variant (i.e., toxoid) of diphtheria toxin. In one embodiment, it is isolated from cultures of *Corynebacterium diphtheria* strain C7 (β197) grown in casamino acids and yeast extract-based medium. In another embodiment, $CRM_{197}$ is prepared recombinantly in accordance with the methods described in U.S. Pat. No. 5,614,382. Typically, $CRM_{197}$ is purified through a combination of ultra-filtration, ammonium sulfate precipitation, and ion-exchange chromatography. In some embodiments, $CRM_{197}$ is prepared in *Pseudomonas fluorescens* using PFENEX EXPRESSION TECHNOLOGY (Pfenex Inc., San Diego, CA).

Other suitable carrier proteins include additional inactivated bacterial toxins such as DT (Diphtheria toxoid), TT (tetanus toxid) or fragment C of TT, pertussis toxoid, cholera toxoid (e.g., as described in International Patent Application Publication No. WO 2004/083251), *E. coli* LT, *E. coli* ST, and exotoxin A from *Pseudomonas aeruginosa*. Bacterial outer membrane proteins such as outer membrane complex c (OMPC), porins, transferrin binding proteins, pneumococcal surface protein A (PspA; See International Application Patent Publication No. WO 02/091998), pneumococcal adhesin protein (PsaA), C5a peptidase from Group A or Group B *streptococcus*, or *Haemophilus influenzae* protein D, pneumococcal pneumolysin (Kuo et al., 1995, Infect Immun 63; 2706-13) including ply detoxified in some fashion for example dPLY-GMBS (See International Patent Application Publication No. WO 04/081515) or dPLY-formol, PhtX, including PhtA, PhtB, PhtD, PhtE and fusions of Pht proteins for example PhtDE fusions, PhtBE fusions (See International Patent Application Publication Nos. WO 01/98334 and WO 03/54007), can also be used. Other proteins, such as ovalbumin, keyhole limpet hemocyanin (KLH), bovine serum albumin (BSA) or purified protein derivative of tuberculin (PPD), PorB (from *N. meningitidis*), PD (*Haemophilus influenzae* protein D; see, e.g., European Patent No. EP 0 594 610 B, or immunologically functional equivalents thereof, synthetic peptides (See European Patent Nos. EP0378881 and EP0427347), heat shock proteins (See International Patent Application Publication Nos. WO 93/17712 and WO 94/03208), pertussis proteins (See International Patent Application Publication No. WO 98/58668 and European Patent No. EP0471177), cytokines, lymphokines, growth factors or hormones (See International Patent Application Publication No. WO 91/01146), artificial proteins comprising multiple human CD4+ T cell epitopes from various pathogen derived antigens (See Falugi et al., 2001, Eur J Immunol 31:3816-3824) such as N19 protein (See Baraldoi et al., 2004, Infect Immun 72:4884-7), iron uptake proteins (See International Patent Application Publication No. WO 01/72337), toxin A or B of *C. difficile* (See International Patent Publication No. WO 00/61761), and flagellin (See Ben-Yedidia et al., 1998, Immunol Lett 64:9) can also be used as carrier proteins.

Other DT mutants can be used, such as $CRM_{176}$, $CRM_{228}$, $CRM_{45}$ (Uchida et al., 1973, J Biol Chem 218:3838-3844); $CRM_9$, $CRM_{45}$, $CRM_{102}$, $CRM_{103}$ and $CRM_{107}$ and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or 4,950,740; mutation of at least one or more residues Lys 516, Lys 526, Phe 530 and/or Lys 534 and other mutations disclosed in U.S. Pat. No. 5,917,017 or 6,455,673; or fragments disclosed in U.S. Pat. No. 5,843,711.

V. Sublimative Drying

Lyospheres may be prepared, for example, by lyophilization or radiant energy vacuum (REV) dehydration (microwave vacuum-drying) in a traveling wave format, Spray freeze-drying, Vacuum Drying, RF Drying etc. in a continuous or semi-continuous mode. See e.g., Encyclopedia of Agriculture, Food, and Biological Engineering. Marcel Dekker, Inc or Xu & Sunada, Chem Pharm Bull (Tokyo) 55(11): 1545-50 (2007).

Lyospheres can be made, for example, by loading an aliquot of an aqueous solution comprising one or more polysaccharide serotypes or carrier protein in the form of a droplet (e.g., about 20, 50, 100 or 250 microliters) onto a solid, flat surface in such a way that the droplet remains intact. In an embodiment of the invention, the surface is a plate, e.g., a metal plate, e.g. at a temperature of about −180° C. to about −196° C. or about −180° C. to about −273° C. For example, in an embodiment of the invention, the aqueous solution is loaded onto the surface by way of a dispensing tip. In an embodiment of the invention, the aqueous solution is dispensed at a dispensing speed of about 3 ml/min to about 75 ml/min, about 5 ml/min to about 75 ml/min; about 3 ml/min to about 60 ml/min, about 20 ml/min to about 75 ml/min; and about 20 ml/min to about 60 ml/min. In an embodiment of the invention, the aqueous solution that is dispensed is 250 microliters and the dispensing speed is between about 5 mL/min to about 75 mL/min, or wherein the aliquot is 100 microliters and the dispensing speed is between about 3 mL/min to about 60 mL/min. In an embodiment of the invention, the gap between a dispensing tip and the surface onto which the aqueous solution is dispensed is about 0.1 cm or more (e.g., about 0.5 cm or between 0.1 cm and 1 cm or between 0.1 cm and 0.75 cm). Once on the surface, the aqueous solution is frozen and then subjected to sublimative drying by lyophilization. Methods for making lyospheres are known in the art. See e.g., U.S. Pat. No. 5,656,597; WO2013066769; WO2014093206; WO2015057540; WO2015057541 or WO2015057548.

VI. Polysaccharide-Protein Conjugation

The purified polysaccharides are chemically activated to introduce functionalities capable of reacting with the carrier protein. Once activated, each capsular polysaccharide is separately conjugated to a carrier protein to form a glycoconjugate according to the method of the present invention.

In one embodiment, the chemical activation of the polysaccharides may be achieved by means described in U.S. Pat. Nos. 4,365,170; 4,673,574; and, 4,902,506. Briefly, the pneumococcal polysaccharide is reacted with an oxidizing agent, for example, a periodate-based oxidizing agent such as sodium periodate, potassium periodate, or periodic acid, resulting in random oxidative cleavage of vicinal hydroxyl groups to generate reactive aldehyde groups.

Direct aminative coupling of the oxidized polysaccharide to primary amine groups on the protein carrier (mainly lysine residues) may be accomplished by reductive amination. For example, conjugation may be carried out in an aqueous solution or in an organic solvent such as dimethylsulfoxide (DMSO). See, e.g., US2015/0231270 A1, EP 0471 177 B1, US2011/0195086 A1. At the conclusion of the conjugation reaction, unreacted aldehydes are capped by addition of a strong reducing agent, such as sodium borohydride.

In one embodiment, the chemical activation of the polysaccharides and subsequent conjugation to the carrier protein are achieved by means described in U.S. Pat. Nos. 4,365,170, 4,673,574 and 4,902,506. Briefly, the polysaccharide is reacted with a periodate-based oxidizing agent such as sodium periodate, potassium periodate, or periodic acid resulting in random oxidative cleavage of vicinal hydroxyl groups to generate reactive aldehyde groups.

Direct aminative coupling of the oxidized polysaccharide to primary amine groups on the protein carrier (mainly lysine residues) may then be accomplished by reductive amination. For example, conjugation is carried out by reacting a mixture of the activated polysaccharide and carrier protein with a reducing agent such as sodium cyanoborohydride in the presence of nickel. The conjugation reaction may be carried out in aqueous solution or in an organic solvent such as dimethylsulfoxide (DMSO). See, e.g., US2015/0231270 A1, EP 0471 177 B1, US2011/0195086 A1. At the conclusion of the conjugation reaction, unreacted aldehydes are optionally reduced by addition of a strong reducing agent, such as sodium borohydride.

In one embodiment, prior to formulation, each pneumococcal capsular polysaccharide is individually purified from S. pneumoniae, activated to form reactive aldehydes, and then covalently conjugated to a carrier protein using reductive amination with sodium cyanoboroydride in the presence of nickel. Nickel forms complexes with residual, interfering cyanide from the sodium cyanoborohydride reducing agent used for reductive amination. Thus, nickel may be used in the methods herein for greater conjugation reaction efficiency and to aid in free cyanide removal.

Transition metals are known to form stable complexes with cyanide and are known to improve reductive methylation of protein amino groups and formaldehyde with sodium cyanoborohydride. See Gidley et al., *Biochem J.* 1982, 203: 331-334; Jentoft et al. *Anal Biochem.* 1980, 106: 186-190. However, Applicants surprisingly found that by complexing residual, interfering cyanide, the addition of nickel increases the consumption of protein during the conjugation of and leads to formation of larger, potentially more immunogenic conjugates.

Variability in free cyanide levels in commercial sodium cyanoborohydride reagent lots may lead to inconsistent conjugation performance, resulting in variable conjugate attributes, including molecular mass and polysaccharide-to-protein ratio. The addition of nickel to the conjugation reaction reduces the level of free cyanide and thus improves the degree of lot-to-lot conjugate consistency.

In another embodiment, the conjugation method may employ activation of polysaccharide with 1-cyano-4-dimethylamino pyridinium tetrafluoroborate (CDAP) to form a cyanate ester. The activated saccharide may be coupled directly to an amino group on the carrier protein.

In an alternative embodiment, a reactive homobifunctional or heterobifunctional group may be introduced on the activated polysaccharide by reacting the cyanate ester with any of several available modalities. For example, cystamine or cysteamine may be used to prepare a thiolated polysaccharide which could be coupled to the carrier via a thioether linkage obtained after reaction with a maleimide-activated carrier protein (for example using GMBS) or a haloacetylated carrier protein (for example using iodoacetimide [e.g. ethyl iodoacetimide HCl] or N-succinimidyl bromoacetate or SIAB, or SIA, or SBAP). Such conjugates are described in International Patent Application Publication Nos. WO 93/15760, WO 95/08348 and WO 96/29094; and Chu et al., 1983, Infect. Immunity 40:245-256.

Other suitable conjugation methods use carbodiimides, hydrazides, active esters, norborane, p-nitrobenzoic acid, N-hydroxysuccinimide, S—NHS, EDC, and/or TSTU. Many are described in International Patent Application Publication No. WO98/42721. Conjugation may involve a carbonyl linker which may be formed by reaction of a free hydroxyl group of the saccharide with CDI (See Bethell et al., 1979, J. Biol. Chem. 254:2572-4; Hearn et al., 1981, J. Chromatogr. 218:509-18) followed by reaction with carrier protein to form a carbamate linkage. This chemistry consists of reduction of the anomeric terminus of a carbohydrate to form a primary hydroxyl group followed by reaction of the primary hydroxyl with CDI to form a carbamate intermediate and subsequent coupling to protein carrier amino groups. The reaction may require optional protection/deprotection of other primary hydroxyl groups on the saccharide.

The following examples are intended to promote a further understanding of the present invention.

Example 1

Preparation of *S. Pneumoniae* Capsular Polysaccharides 6A, 6B, 7F, 18C, 19A, 19F, and 23F Methods of culturing pneumococci are well known in the art. See, e.g., Chase, 1967, Methods of Immunology and Immunochemistry 1:52. Methods of preparing pneumococcal capsular polysaccharides are also well known in the art. See, e.g., European Patent No. EP0497524. Isolates of pneumococcal subtypes are available from the American Type Culture Collection (Manassas, VA). The bacteria are identified as encapsulated, non-motile, Gram-positive, lancet-shaped diplococci that are alpha-hemolytic on blood-agar. Subtypes can be differentiated on the basis of Quelling reaction using specific antisera. See, e.g., U.S. Pat. No. 5,847,112.

Cell banks representing each of the *S. pneumococcus* serotypes present are obtained from the Merck Culture Collection (Rahway, NJ) in a frozen vial. A thawed seed culture is transferred to the seed fermentor containing a pre-sterilized growth media appropriate for *S. pneumoniae*. The culture is grown in the seed fermentor with temperature and pH control. The entire volume of the seed fermentor is transferred to a production fermentor containing pre-sterilized growth media. The production fermentation is the final cell growth stage of the process. Temperature, pH, and the agitation rate are controlled.

The fermentation process is terminated via the addition of an inactivating agent. After inactivation, the solution is transferred to the inactivation tank where it is held at controlled temperature and agitation. Cell debris is removed using a combination of centrifugation and filtration. The solution is ultrafiltered and diafiltered. The solution is then subjected to solvent-based fractionations that remove impurities and recover polysaccharide.

Example 2

Polysaccharide size reduction and activation is performed as follows.

About 6 g of purified pneumococcal capsular polysaccharide (Ps) powder is dissolved in water for injection (WFI) to a target concentration of approximately 4 g/L at room temperature. The solution is then 0.45-micron filtered to reduce bioburden. The Ps concentration of the filtered Ps solution is determined by HPSEC UV-MALS-RI.

For all serotypes except serotypes 18C and 19A, the solution is diluted to approximately 2.5 g/L and then homogenized to reduce the molecular mass of the Ps using a GEA-Niro Soavi Panda 2K homogenizer. All serotypes, except serotype 19A, were homogenized to reduce the molecular mass of the polysaccharide. Serotype 19A was not size reduced due to its relatively low starting size. Homogenization pressure and number of passes through the homogenizer were controlled to serotype-specific targets (150-1000 bar; 4-7 passes) to achieve a serotype-specific molecular mass. Size-reduced polysaccharide was 0.2-micron filtered and then concentrated and diafiltered against water using a 10 kDa NMWCO tangential flow ultrafiltration membrane. Temperature is controlled during homogenization using a chilled water supply to a heat exchanger at the outlet of the homogenizer.

Acid hydrolysis is used instead of homogenization to reduce the molecular mass of the serotype 18C Ps. The temperature of the filtered serotype 18C Ps solution is increased to approximately 96° C. for Lot A and 90° C. for Lot B. The solution is then adjusted with glacial acetic acid (17.4 M) to target a final concentration of 0.2 M and held for approximately 180 minutes for Lot A and 160 minutes for Lot B. 1.5 M potassium phosphate, pH 7.0 is added to a final concentration of 0.46 M to stop the acid hydrolysis by increasing the solution pH, and the solution is then cooled to room temperature.

Serotype 19A is not 0.45-micron filtered or size-reduced. Due to its relatively low starting size, size reduction is not required. Following dissolution, serotype 19A is 0.22-micron filtered as described in the next paragraph.

Each solution is then filtered using a 0.22-micron filter to reduce bioburden prior to the Ultrafiltration 1 step. The filtered Ps is concentrated to approximately 10 g/L using a 10 kDa NMWCO tangential flow ultrafiltration membrane and then diafiltered against 6 diavolumes of WFI at ambient temperature, generating the Ultrafiltration 1 process intermediate (UF1-FR). Serotype 18C used a 5 kDa NMWCO membrane instead of a 10 kDa NMWCO membrane to improve Ps recovery by retaining lower molecular weight Ps generated by acid hydrolysis. The Ps concentration of the UF1-FR is determined by HPSEC UV-MALS-RI. WFI is added to the UF1-FR to achieve a Ps concentration of approximately 10 g/L prior to Ps activation.

2 M sodium acetate buffer is then added to control the pH of the activation reaction step. The sodium acetate concentration and pH, and temperature during the Ps activation reaction are controlled to specific values for each serotype (Table 2).

The periodate activation is initiated by adding a 100 mM sodium metaperiodate solution to the solution on a basis of moles of periodate per mole of PnPs repeating unit (RU). During the activation, vicinal diols are oxidized to reactive aldehydes over a serotype-specific reaction time. This reaction generated the activated product (AP) process intermediate. The amount of sodium metaperiodate charged and the reaction time are controlled to specific values for each serotype (Table 1).

TABLE 2

Serotype-Specific Activation Parameters

| Serotype | MBC Lot Number | Activation Temperature (° C.) | Sodium Acetate Concentration (mM) | pH of 2M Sodium Acetate Stock Buffer | Sodium Periodate Charge (meq) | Activation Reaction Time (hrs) |
|---|---|---|---|---|---|---|
| 6A | Lot A<br>Lot B | 22 | 50 | 5.0 | 0.10 | 2 |
| 6B | Lot A<br>Lot B | 22 | 50 | 5.0 | 0.10 | 2 |
| 7F | Lot A<br>Lot B | 4 | 50 | 5.0 | 0.24 | 4 |
| 18C | Lot A<br>Lot B | 22 | 50 | 5.0 | 0.14 | 2 |
| 19A | Lot A<br>Lot B | 22 | 50 | 5.0 | 0.26 | 20 |
| 19F | Lot A<br>Lot B | 4 | 50 | 5.0 | 0.10 | 4 |
| 23F | Lot A<br>Lot B | 22 | 50 | 5.0 | 0.15 | 4 |

Following Ps activation, the solution is diafiltered against 6 diavolumes of 10 mM potassium phosphate, pH 6.4, followed by an additional 6 diavolumes of WFI using a 10 kDa NMWCO tangential flow ultrafiltration membrane at 2-8° C. Serotype 18C used a 5 kDa NMWCO membrane instead of a 10 kDa NMWCO membrane to improve Ps recovery by retaining lower molecular weight Ps generated by acid hydrolysis. The solution is then concentrated, generating the Ultrafiltration 2 process intermediate (UF2-FR). The Ps concentration of the UF2-FR is determined by HPSEC UV-MALS-RI. The extent of activation is determined by derivatizing a UF2-FR sample with thiosemicarbazide, then detecting thiosemicarbazone by HPSEC with UV detection.

Example 3

Preparation of $CRM_{197}$ Carrier Protein may be performed as follows.

Frozen, purified $CRM_{197}$, obtained through expression in *Pseudomonas fluorescens* as previously described (See International Patent Application Publication No. WO 2012/173876) is diafiltered against 10 diavolumes of 2 mM phosphate, pH 7.2 buffer using a 5 kDa NMWCO tangential flow ultrafiltration membrane and 0.22-micron filtered. In particular embodiments, 5 mM potassium phosphate, pH 6.4 (5 mM sodium phosphate, pH 7.0 is used for serotype 18C. The diafiltered solution is diluted in water with sucrose for a final concentration of between 1.0 and 5.3% (w/v). Table 3 below provides representative sucrose concentrations for $CRM_{197}$ for conjugation against particular serotype polysaccharides.

Example 4

Lyosphere production of Polysaccharide (Ps) and $CRM_{197}$ (Pr) is as follows.

Prior to lyophilization, the $CRM_{197}$ and Ps solutions are diluted as described below.

In some embodiments, the $CRM_{197}$ solution is diluted to a protein concentration of 6.0 mg/mL using WFI, 5 mM sodium phosphate, pH 6.4 (pH 7.0 for serotype 18C), and a freshly prepared 30% w/v sucrose solution in WFI. The UF2-FR Ps solution is diluted to a Ps concentration of 6.0 mg/mL using WFI and a freshly prepared 30% w/v sucrose solution in WFI.

In some embodiments, the $CRM_{197}$ solution is diluted to a protein concentration of 6.0 mg/mL using WFI, 2 mM sodium phosphate, pH 7.2, and a freshly prepared 50% w/v sucrose solution in WFI. The UF2-FR Ps solution is diluted to a Ps concentration of 6.0 mg/mL using WFI and a freshly prepared 50% w/v sucrose solution in WFI.

Serotype-specific sucrose and phosphate concentrations are used (Table 3). The diluted $CRM_{197}$ and UF2-FR solutions are processed into lyospheres as follows.

TABLE 3

Serotype-Specific Lyophilization Parameters

| Serotype | MBC Lot Number | Sucrose Concentration in CRM197 Solution Prior to Lyophilization (% w/v) | Sodium Phosphate Concentration in CRM197 Solution Prior to Lyophilization (mM) | Sucrose Concentration in UF2-FR Ps Solution Prior to Lyophilization (% w/v) |
|---|---|---|---|---|
| 6A | Lot A | 4.0 | 3.8 | 4.0 |
|    | Lot B | 1.0 | 1.25 | 5.0 |
| 6B | Lot A | 1.0 | 2.3 | 3.5 |
|    | Lot B |     | 1.25 | 5.0 |
| 7F | Lot A | 5.3 | 2.4 | 5.3 |
|    | Lot B | 1.0 | 1.25 | 5.0 |
| 18C | Lot A | 2.4 | 2.8 | 4.0 |
|    | Lot B | 1.0 | 1.25 | 5.0 |
| 19A | Lot A | 1.0 | 1.6 | 3.0 |
|    | Lot B |     | 1.25 | 5.0 |
| 19F | Lot A | 1.0 | 2.3 | 5.0 |
|    | Lot B |     | 1.25 |     |
| 23F | Lot A | 3.0 | 1.7 | 3.0 |
|    | Lot B | 1.0 | 1.25 | 5.0 |

Example 5

This example shows development of lyophilizer conditions for producing polysaccharide (Ps) and $CRM_{197}$ (Pr, CRM) lyospheres.

Discrete solutions of CRM and activated polysaccharides from serotypes 6A and 23F were prepared as described in Examples 3 and 4 and having Ps, CRM, and sucrose concentrations as shown in the tables in this example.

A modified Biomek FX pipetting robot (Cryomek) is used to dispense 50 μL aliquots of the solutions onto the flat freezing surface of the Cryomek. A shoveling mechanism may be used to dispense the beads onto a small cold container without causing any fractures. After completing the cycle for each different solution, the beads are transferred into an intermediate storage container and kept at −70° C. until sublimative drying in a lyophilizer or by microwave vacuum drying. For lyophilizer drying, beads are dispensed in a single layer into the drying trays. Cabinet pressure, shelf temperature and cycle time are set up. After drying the beads, the lyospheres are stored at 2-8° C. (See Example 5 for specific parameters)

The preliminary drying cycle (Lyo1) took 18 hours, as shown in Table 4.1. Residual moisture content of the lyospheres, determined by Karl Fisher titration, is shown on Table 4.2.

TABLE 4.1

Lyo1 Cycle Parameters

| Drying | Cabinet Pressure (mTorr) | Shelf Temperature (° C.) | Time (hours) |
|---|---|---|---|
| Primary | 30 | 15 | 18 |

TABLE 4.2

Karl Fisher Analysis for Lyospheres dried in Lyo1.

| Sample ID | Active material concentration (mg/mL) | Sucrose (w/v) | Residual moisture (%) |
|---|---|---|---|
| 6A Ps | 6 | 4 | 5.81 |
| CRM for 6A Ps | 6 | 4 | 6.16 |
| 23F Ps | 6 | 3 | 7.81 |
| CRM for 23F Ps | 6 | 3 | 10.4 |

The results show high moisture content in the lyospheres. In addition, lyospheres were very fragile and hydroscopic. Solids content was increased by increasing polyscaccharide, protein, and sucrose concentrations, as shown in Table 5.2. The drying cycle was modified (Lyo 2) by adding a secondary drying cycle and increasing the primary drying time, as shown in Table 5.1.

TABLE 5.1

Lyo2 Cycle Parameters

| Drying | Cabinet Pressure (mTorr) | Shelf Temperature (° C.) | Time (hours) |
|---|---|---|---|
| Primary | 30 | 15 | 40 |
| Secondary | 30 | 30 | 5 |

TABLE 5.2

Karl Fisher Analysis for Lyospheres Dried in Lyo2

| Sample ID | Active material concentration (mg/mL) | Sucrose (w/v) | Residual moisture (%) |
|---|---|---|---|
| 6A Ps | 6 | 4 | 2.09 |
| CRM for 6A Ps | 6 | 4 | 1.72 |
| 6A Ps-2 | 9 | 6 | 1.80 |
| CRM-2 for 6A Ps | 9 | 6 | 2.49 |
| CRM-3 for 6A Ps | 12 | 8 | 1.92 |
| 23F Ps | 6 | 3 | 3.4 |
| CRM for 23F Ps | 6 | 3 | 2.96 |
| 23F Ps-2 | 8.4 | 4.2 | 3.16 |
| CRM-2 for 23F Ps | 8.4 | 4.2 | 3.78 |
| CRM-3 for 23F Ps | 15 | 7.5 | 2.51 |

Residual moisture content from Lyo2 was significantly lower than from Lyo1 due to improved drying cycle. Secondary drying improves removal of bound moisture that is still present in the product even after all ice has sublimated. The secondary drying required a higher temperature (30° C.) than primary drying (15° C.).

At this point, the Lyophilizer total drying cycle time was 45 hours. Several parameters such as pressure and temperature were changed in order to reduce even more the drying cycle time (method: Lyo 3) Tables 6.1 and 6.2.

TABLE 6.1

LyophilizerDrying Cycle with increased Cabinet Pressure and Shelf Temperature (Lyo3)

| Drying | Cabinet Pressure (mTorr) | Shelf Temperature (° C.) | Time (hours) |
|---|---|---|---|
| Primary | 55 | 20 | 18 |
| Secondary | 55 | 30 | 5 |

TABLE 6.2

Karl Fisher Analysis for Lyospheres Dried in Lyo3

| Sample ID | Active material concentration (mg/mL) | Sucrose (w/v) | Residual moisture (%) |
|---|---|---|---|
| 6A Ps | 9 | 6 | 1.61 |
| CRM for 6A Ps | 12 | 8 | 1.64 |
| 23F Ps | 8.4 | 4.2 | 2.64 |
| CRM for 23F Ps | 8.4 | 4.2 | 1.87 |

Example 6

This example shows development of radiant energy vacuum (REV) dehydration (microwave vacuum drying (MVD)) conditions for producing polysaccharide (Ps) and CRM$_{197}$ (Pr; CRM) lyospheres.

Solutions of CRM and activated polysaccharides from serotypes 6A and 23F were prepared as described in Examples 3 and 4 and having Ps, CRM, and sucrose concentrations as shown in the Tables 7.1 and 7.2.

A modified Biomek FX pipetting robot (Cryomek) is used to dispense 50 μL aliquots of the solution onto the flat freezing surface of the Cryomek. A shoveling mechanism may be used to dispense the beads onto a small cold container without causing any fractures. After completing the cycle for each different solution, the beads are transferred into an intermediate storage container and kept at −70° C. until sublimative drying in a lyophilizer or by microwave vacuum drying. For microwave drying, beads were dispensed in single layers into the containers. Power, pressure and cycle time were set up. After drying the beads, lyospheres were stored at 2-8° C. (See Example 6 for specific parameters).

Two different MVD cycles were tested to dry the beads. For both cycles, the pressure was kept in the range of 50 to 60 mTorr. The temperature was dependent on how much power was applied, staying in the range of 25 to 30° C.

TABLE 7.1

Microwave Vacuum Drying Cycle, MVD1 and MVD2

| Drying Cycle | Temperature (° C.) | Pressure (mTorr) | Power (W) | Time |
|---|---|---|---|---|
| MVD1 | 20-30 | 50-60 | 400-600 | 4 hours 30 minutes |
| MVD2 | 20-30 | 50-60 | 400-2000 | 6 hours 10 minutes |

TABLE 7.2

Karl Fisher Analysis for Lyospheres Dried in MVD1 and MVD2.

| Sample | Active material concentration (mg/mL) | Sucrose (w/v) | MDV1 Residual Moisture % | MDV2 Residual Moisture (%) |
|---|---|---|---|---|
| 6A Ps | 9 | 6 | 3.30 | 2.38 |
| CRM for 6A Ps | 12 | 8 | 2.94 | 1.72 |
| 23F Ps | 8.4 | 4.2 | 3.80 | 2.80 |
| CRM for 23F Ps | 8.4 | 4.2 | 3.01 | 1.83 |

MVD1 cycle took 4 hours and 30 minutes but it was not enough to reduce residual moisture content up to 2%. MVD2 cycle took longer with higher power and, therefore, it provided residual moisture content that was significantly lower.

Example 7

In preparation for conjugation, polysaccharide (Ps) lyospheres and CRM$_{197}$ protein (Pr) lyospheres are combined targeting a specific ratio of Ps to Pr (Ps:Pr) and final Ps concentration to provide a lyosphere mixture that is dissolved in anhydrous DMSO as above. Sodium cyanoborohydride is added to this Ps:Pr blend and the solution is incubated at the required conjugation temperature for the appropriate reaction time, both of which are specific for the Ps serotypes being conjugated to the Pr. The size of the resulting conjugate size has been shown to be significantly affected by Ps concentration.

A solution of sodium cyanoborohydride in WFI is prepared, and 1.0 meq of sodium cyanoborohydride (1.0 mole of sodium cyanoborohydride per mole of Ps repeating unit) is added to the solution. The molarity of the sodium cyanoborohydride solution (Table 8) is based on the target of approximately 0.5% total water content of the solution during conjugation. The solution is allowed to react at serotype-specific temperature for a serotype-specific duration (Table 8) generating the Conjugated Product intermediate (CP).

A solution of sodium borohydride in WFI is prepared, and 2.0 meq of sodium borohydride (relative to Ps repeating units) is added to the solution. The molarity of the sodium borohydride solution (Table 2) is based on the target of approximately 1.0% total water content in the solution after borohydride addition. The solution is allowed to react for 3 hours (except for at V1147FPB1401 which is allowed to react for 2 hours) at ambient temperature, generating the Conjugate Product Quenched intermediate (CPQ).

TABLE 8

Serotype-Specific DMSO Conjugation Parameters

| Serotype | MBC Lot Number | Ps Conc. during Conj. (g/L) | Ps:CRM197 Mass Ratio during Conjugation (w/w) | Conj. Temp. (C) | Sodium Cyanoborohydride Solution Conc. (mM) | Conj. Reaction Time (hr) | Sodium Borohydride Solution Conc. (mM) |
|---|---|---|---|---|---|---|---|
| 6A | Lot A | 1.1 | 1.4 | 23.0 | 321 | 48 | 643 |
|  | Lot B | 1.5 | 1.4 | 22.0 | 493 | 15 | 377 |
| 6B | Lot A | 1.6 | 1.35 | 18.5 | 467 | 3.5 | 935 |
|  | Lot B | 1.85 | 1.35 | 22.0 | 591 | 3 | 1081 |
| 7F | Lot A | 1.5 | 2.0 | 23.0 | 253 | 4 | 506 |
|  | Lot B | 2.6 | 1.5 | 22.0 | 465 | 4 | 878 |

TABLE 8-continued

Serotype-Specific DMSO Conjugation Parameters

| Serotype | MBC Lot Number | Ps Conc. during Conj. (g/L) | Ps:CRM197 Mass Ratio during Conjugation (w/w) | Conj. Temp. (C) | Sodium Cyanoborohydride Solution Conc. (mM) | Conj. Reaction Time (hr) | Sodium Borohydride Solution Conc. (mM) |
|---|---|---|---|---|---|---|---|
| 18C | Lot A | 3.0 | 1.5 | 23.0 | 632 | 1 | 1265 |
| | Lot B | 3.1 | 1.5 | 22.0 | 672 | 2 | 1307 |
| 19A | Lot A | 3.0 | 1.3 | 18.5 | 1014 | 1.5 | 2029 |
| | Lot B | 3.8 | 1.33 | 22.0 | 1285 | 1.5 | 2570 |
| 19F | Lot A | 1.6 | 1.2 | 18.5 | 541 | 9 | 1082 |
| | Lot B | 2.0 | 1.2 | 22.0 | 720 | 8 | 1353 |
| 23F | Lot A | 2.25 | 1.25 | 23.0 | 584 | 8 | 1168 |
| | Lot B | 2.45 | 1.25 | 22.0 | 660 | 4 | 1272 |

The conjugation solutions are then diluted to 20% or less (v/v) anhydrous DMSO by slowly adding the solution to 150 mM sodium chloride (150 mM sodium chloride with 0.025% w/v polysorbate 20 for conjugates in some embodiments). The solution temperature is maintained at less than 15° C. during the dilution step. After about one hour, 1.5 M potassium phosphate, pH 6.0, is added to the solution to a final concentration of 25 mM potassium phosphate. Conjugation performance is assessed by overall Ps and $CRM_{197}$ consumption, conjugate Ps to $CRM_{197}$ ratio, and conjugate molecular weight.

The conjugation solutions are concentrated to approximately 2.5 g/L and diafiltered against 10 diavolumes of 150 mM sodium chloride (for lots in WL00067190) or 25 mM potassium phosphate in 150 mM sodium chloride (for lots in WL00067191) at 2-8° C. using a 30 kDa NMWCO tangential flow ultrafiltration membrane. This generated the Ultrafiltration 3 process intermediate (UF3-FR). The Ps concentration of the UF3-FR is determined by HPSEC UV-MALS-RI.

For 19F in some embodiments, the UF3-FR is 0.22-micron filtered and subsequently incubated at 22° C. for approximately 120 hours.

The UF3-FR solutions are then processed in the Ultrafiltration 4 step. During the Ultrafiltration 4 step in some embodiments, the solutions are concentrated to a Ps concentration of approximately 2.5 g/L and diafiltered against 20 diavolumes of 10 mM L-histidine in 150 mM sodium chloride, pH 7.0 at 2-8° C. using a 300 kDa NMWCO Biomax PES tangential flow ultrafiltration membrane. Serotype 7F used a 100 kDa NMWCO membrane for the Ultrafiltration 4 step. For serotype 6A, 6B, and 18C 1 used, the UF3-FR solutions are concentrated to approximately 3.5 g/L and diafiltered against 10 mM L-histidine in 150 mM sodium chloride, 0.03% w/v PS-20, pH 7.0 at 2-8° C. using a 300 kDa NMWCO Biomax PES tangential flow ultrafiltration membrane. In some embodiments, serotype 7F, 19A, 19F and 23F UF3-FR solutions are concentrated to approximately 2.0 g/L and diafiltered against 10 mM L-histidine in 150 mM sodium chloride, 0.015% w/v PS-20, pH 7.0 at 2-8° C. using a 300 kDa NMWCO UltraCel, regenerated cellulose, tangential flow ultrafiltration membrane. This generated the Ultrafiltration 4 process intermediate (UF4-FR). The Ps concentration of the UF4-FR is determined by HPSEC UV-MALS-RI.

The UF4-FR is 0.22-micron filtered through a PVDF filter. The Ps concentration of the filtrate is determined by HPSEC UV-MALS-RI. If the Ps concentration of the filtrate is greater than 1.0 g/L, the filtrate is then diluted to a Ps concentration of 1.0 g/L with additional 10 mM L-histidine in 150 mM sodium chloride, pH 7.0. This generated the Monovalent Bulk Conjugate intermediate (MBC). The MBC is dispensed into aliquots and frozen at −60° C. to −80° C.

The UF4-FR for serotype 6A, 6B, and 18C is 0.5/0.2-micron filtered through a dual-membrane PES filter. The Ps concentration of the filtrate is determined by HPSEC UV-MALS-RI. If the Ps concentration of the filtrate is greater than 1.0 g/L, the filtrate is then diluted to a Ps concentration of 1.0 g/L with additional 10 mM L-histidine in 150 mM sodium chloride, 0.03% w/v PS-20, pH 7.0. This generated the Monovalent Bulk Conjugate intermediate (MBC). The MBC is dispensed into aliquots and frozen at −60° C. to −80° C.

The UF4-FR for serotype 7F, 19A, 19F, and 23F are 0.22-micron filtered through a PVDF filter. The Ps concentration of the filtrate is determined by HPSEC UV-MALS-RI. If the Ps concentration of the filtrate is greater than 1.0 g/L, the filtrate is then diluted to a Ps concentration of 1.0 g/L with additional 10 mM L-histidine in 150 mM sodium chloride, 0.015% w/v PS-20, pH 7.0. This generated the Monovalent Bulk Conjugate intermediate (MBC). The MBC is dispensed into aliquots and frozen at −60° C. to −80° C.

Example 8

This example shows a method for conjugation of Ps from serotypes 1, 2, 3, 4, 5, 6A, 6B, 6C, 6D, 7B, 7C, 7F, 8, 9N, 9V, 10A, 11A, 12F, 14, 15A, 15B, 15C, 16F, 17F, 18C, 19A, 19F, 20, 21, 22A, 22F, 23A, 23B, 23F, 24F, 27, 28A, 31, 33F, 34, 35A, 35B, 35F, or 38 to $CRM_{197}$ (Pr) using reductive amination in anhydrous DMSO. The different serotype polysaccharides are individually conjugated to purified $CRM_{197}$ carrier protein using a common process flow.

Polysaccharide (Ps) lyospheres and $CRM_{197}$ protein (Pr) lyospheres are combined targeting a specific ratio of Ps to Pr (Ps:Pr) and final Ps concentration to provide a lyosphere mixture that is dissolved in anhydrous DMSO as above. Sodium cyanoborohydride is added to this Ps:Pr reconstituted mixture and the solution is incubated at the required conjugation temperature for the appropriate reaction time, both of which are specific for the Ps serotypes being conjugated to the Pr. The size of the resulting conjugate size has been shown to be significantly affected by Ps concentration.

Reduction with Sodium Borohydride

Sodium borohydride (2 mole per mole of polysaccharide repeating unit) is added following the conjugation reaction and the solution and incubated for 1 hour at 22° C. The solution is diluted into 150 mM sodium chloride, 0.025% (w/v) polysorbate 20, at approximately 4° C. Potassium phosphate buffer is then added to neutralize the pH. The solution is concentrated and diafiltered at approximately 4° C. against 150 mM sodium chloride using a 10 kDa NMWCO tangential flow ultrafiltration membrane.

Final Filtration and Product Storage

Each solution is then concentrated and diafiltered against 10 mM histidine in 150 mM sodium chloride, pH 7.0 at 4° C. using a 300 kDa NMWCO tangential flow ultrafiltration membrane. The retentate solution is 0.22-micron filtered.

Serotype 19F is incubated for approximately 5 days, diafiltered against 10 mM histidine in 150 mM sodium chloride, pH 7.0 at approximately 4° C. using a 300 kDa NMWCO tangential flow ultrafiltration membrane, and 0.22-micron filtered.

Serotype 18C is diafiltered against 10 mM histidine in 150 mM sodium chloride, pH 7.0 at approximately 4° C. using a 300 kDa NMWCO tangential flow ultrafiltration membrane, and 0.22-micron filtered.

The solutions are diluted with additional 10 mM histidine in 150 mM sodium chloride, pH 7.0 and dispensed into aliquots and frozen at ≤−60° C.

Example 9

This example shows formulation of a 15-valent Pneumococcal Conjugate Vaccine with different surfactants and stabilizers.

Pneumococcal polysaccharide-protein conjugates prepared as described above are used for the formulation of a 15-valent pneumococcal conjugate vaccine (PCV15) having serotypes 1, 3, 4, 5, 6A, 6B, 7F, 9V, 14, 18C, 19A, 19F, 22F, 23F, and 33F.

The formulations are prepared using pneumococcal polysaccharide-$CRM_{197}$ conjugates generated by reductive amination in DMSO as discussed previously. The required volumes of bulk conjugates needed to obtain the target final concentration of individual serotype are calculated based on the solution volume and the bulk polysaccharide concentrations. The 15 conjugates are combined with the excipients selected from sodium chloride, L-histidine, pH 5.8 buffer with polysorbate (PS)-20, PS-80, or poloxamer (P)188.

The sterile formulated bulk is mixed gently during and following its blending with bulk Aluminum Phosphate Adjuvant (APA) with or without propylene glycol (PG) and polyethylene glycol 400 ($PEG_{400}$). Two concentrations of conjugates and APA are studied in the various formulations. One contained 8 μg/mL serotype 6B polysaccharide, 4 μg/mL polysaccharide for all other serotypes, and 250 μg/mL APA. The other contained 16 μg/mL serotype 6B polysaccharide, 8 μg/mL polysaccharide for all other serotypes, and 500 μg/mL APA. The formulated vaccines are stored at 2-8° C.

APA is an aqueous suspension of aluminum hydroxyphosphate. APA is manufactured by blending aluminum chloride and sodium phosphate in a 1:1 volumetric ratio to precipitate aluminum hydroxyphosphate. After the blending process, the material is size-reduced with a high-shear mixer to achieve a monodisperse particle size distribution. The product is then diafiltered against physiological saline and steam sterilized.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A method for making a composition comprising one or more *Streptococcus pneumoniae* polysaccharides covalently linked to a carrier protein, the method comprising:
   (a) providing a first lyosphere composition comprising activated *Streptococcus pneumoniae* polysaccharides from one or more *Streptococcus pneumoniae* serotypes and a second lyosphere composition comprising carrier protein,
   wherein the first and second lyosphere compositions are prepared by a sublimative drying process selected from lyophilization and radiant energy vacuum (REV) dehydration comprising: (i) providing a first aqueous solution comprising activated *Streptococcus pneumoniae* polysaccharides from one or more *Streptococcus pneumoniae* serotypes and a second aqueous solution comprising a carrier protein and a buffer, wherein the first aqueous solution comprises about 4% to 6% sucrose and the second aqueous solution comprises about 4% to 8% sucrose, and (ii) subjecting the first and second aqueous solutions to the sublimative drying process to produce the first and second lyosphere compositions;
   (b) combining an amount of the first lyosphere composition and an amount of the second lyosphere composition together to provide a lyosphere mixture having a predetermined ratio of the one or more activated polysaccharides to the carrier protein;
   (c) reconstituting the lyosphere mixture in an organic solvent and mixing to provide a reconstituted mixture; and
   (d) adding a reducing agent to the reconstituted mixture to produce a conjugate solution comprising carrier protein conjugated to the polysaccharides of the one or more *Streptococcus pneumoniae* serotypes, wherein the conjugated carrier protein has a lysine loss value of greater than five (mole/mole).

2. The method of claim 1, wherein the buffer is a Histidine, Succinate, MES, MOPS, HEPES, or Acetate buffer in a pH range of 5.0-7.0.

3. The method of claim 1, wherein the buffer is a Phosphate or a Citrate buffer in a pH range of 5.0-7.0.

4. The method of claim 1, wherein the first and second lyosphere compositions each have a moisture content of less than 6%.

5. The method of claim 1, wherein the organic solvent is dimethyl sulfoxide (DMSO).

6. The method of claim 1, wherein the reconstituting is performed in eight minutes or less and the mixing is performed in 120 minutes or less.

7. The method of claim 1, wherein the conjugate solution comprises polysaccharide conjugated to the carrier protein at a ratio from about 0.6 to about 1.5 polysaccharide to carrier protein on a weight to weight basis.

8. The method of claim 1, wherein the conjugate solution comprises a free polysaccharide amount that is less than about 15% of the total polysaccharide in the solution.

9. The method of claim 1, wherein the one or more *Streptococcus pneumoniae* serotypes are selected from the group consisting of *Streptococcus pneumoniae* serotypes 1, 2, 3, 4, 5, 6A, 6B, 6C, 6D, 6E, 6G, 6H, 7F, 7A, 7B, 7C, 8, 9A, 9L, 9N, 9V, 10F, 10A, 10B, 10C, 11F, 11A, 11B, 11C, 11D, 11E, 12F, 12A, 12B, 13, 14, 15F, 15A, 15B, 15C, 16F, 16A, 17F, 17A, 18F, 18A, 18B, 18C, 19F, 19A, 19B, 19C, 20A, 20B, 21, 22F, 22A, 23F, 23A, 23B, 24F, 24A, 24B, 25F, 25A, 27, 28F, 28A, 29, 31, 32F, 32A, 33F, 33A, 33B, 33C, 33D, 33E, 34, 35F, 35A, 35B, 35C, 36, 37, 38, 39, 40, 41F, 41A, 42, 43, 44, 45, 46, 47F, 47A, 48, CWPS1, CWPS2, and CWPS3.

10. The method of claim 1, wherein the carrier protein is an inactivated bacterial toxoid selected from the group consisting of tetanus toxoid, diphtheria toxoid, pertussis toxoid, bacterial cytolysins, and pneumolysin.

11. The method of claim 10, wherein the diphtheria toxoid is $CRM_{197}$.

12. The method of claim 1, wherein the conjugate solution is sterile filtered.

13. The method claim 1, wherein the *Streptococcus pneumoniae* polysaccharides are activated by reacting with an oxidizing agent.

* * * * *